(12) United States Patent
Molt et al.

(10) Patent No.: US 8,691,401 B2
(45) Date of Patent: Apr. 8, 2014

(54) BRIDGED BENZIMIDAZOLE-CARBENE COMPLEXES AND USE THEREOF IN OLEDS

(75) Inventors: Oliver Molt, Weinheim (DE); Christian Lennartz, Schifferstadt (DE); Korinna Dormann, Bad Duerkheim (DE); Evelyn Fuchs, Mannheim (DE); Thomas Gessner, Heidelberg (DE); Nicolle Langer, Heppenheim (DE); Soichi Watanabe, Mannheim (DE); Christian Schildknecht, Mannheim (DE); Gerhard Wagenblast, Wachenheim (DE)

(73) Assignee: BASF SE, Ludwigshafen (DE)

( * ) Notice: Subject to any disclaimer, the term of this patent is extended or adjusted under 35 U.S.C. 154(b) by 374 days.

(21) Appl. No.: 13/087,954

(22) Filed: Apr. 15, 2011

(65) Prior Publication Data

US 2011/0253988 A1    Oct. 20, 2011

Related U.S. Application Data

(60) Provisional application No. 61/324,771, filed on Apr. 16, 2010.

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/102; 257/103; 257/E51.044; 548/108

(58) Field of Classification Search
None
See application file for complete search history.

(56) References Cited

U.S. PATENT DOCUMENTS

| | | | |
|---|---|---|---|
| 2006/0251923 A1* | 11/2006 | Lin et al. | 428/690 |
| 2007/0224446 A1 | 9/2007 | Nakano et al. | |
| 2008/0018221 A1 | 1/2008 | Egen et al. | |
| 2009/0017331 A1 | 1/2009 | Iwakuma et al. | |
| 2009/0054657 A1 | 2/2009 | Molt et al. | |
| 2009/0134784 A1 | 5/2009 | Lin et al. | |
| 2009/0153034 A1 | 6/2009 | Lin et al. | |
| 2009/0284138 A1 | 11/2009 | Yasukawa et al. | |

FOREIGN PATENT DOCUMENTS

| | | |
|---|---|---|
| EP | 1 097 981 A2 | 5/2001 |
| EP | 1 537 761 | 6/2005 |
| EP | 1 786 050 A1 | 5/2007 |
| EP | 1 837 926 B1 | 9/2007 |
| JP | 2008-21687 | 1/2008 |
| JP | 2008-66569 | 3/2008 |
| JP | 2008-74939 | 4/2008 |
| JP | 2008-84913 | 4/2008 |
| JP | 2008-207520 | 9/2008 |
| JP | 2009-21336 | 1/2009 |
| JP | 2009-59767 | 3/2009 |
| JP | 2009-114369 | 5/2009 |
| JP | 2009-114370 | 5/2009 |
| JP | 2009-135183 | 6/2009 |
| JP | 2009-170764 | 7/2009 |
| JP | 2009-182298 | 8/2009 |

(Continued)

OTHER PUBLICATIONS

International Preliminary Report on Patentability and Written Opinion of the International Searching Authority issued Sep. 8, 2011, in PCT/IB2011/051647.

(Continued)

*Primary Examiner* — Michael H Wilson
(74) *Attorney, Agent, or Firm* — Oblon, Spivak, McClelland, Maier & Neustadt, L.L.P.

(57) ABSTRACT

The present invention concerns a metal-carbene complex of the general formula (I)

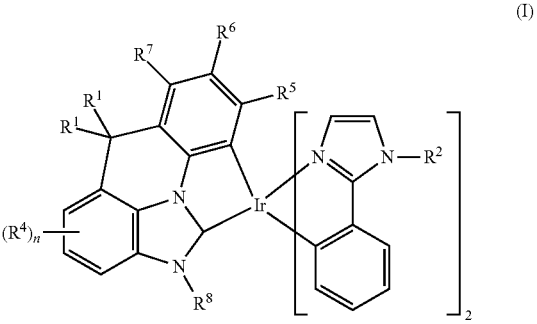

in which $R^5$ and $R^6$ together, or $R^6$ and $R^7$ together, a unit of the formula:

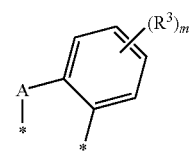

in which * denotes the connection to the carbon atoms of the benzene ring bearing the $R^5$ and $R^6$ radicals or $R^6$ and $R^7$ radicals, and the oxygen atom is connected to the carbon atom bearing the $R^5$, $R^6$ or $R^7$ radical, and A is oxygen or sulfur.

The present invention further concerns light-emitting layer comprising at least one metal-carbene complex according to the present invention and an organic light-emitting diode comprising a light-emitting layer according to the present invention, a device selected from the group consisting of stationary visual display units, mobile visual display units and illumination means and the use of a metal-carbene complex according to the present invention in organic light-emitting diodes, especially as emitter, matrix material, charge carrier material and charge blocker material.

15 Claims, No Drawings

(56) References Cited

FOREIGN PATENT DOCUMENTS

| | | |
|---|---|---|
| JP | 2009-267255 | 11/2009 |
| JP | 2010-21336 | 1/2010 |
| JP | 2010-40830 | 2/2010 |
| JP | 2010-114180 | 5/2010 |
| JP | 2010-135467 | 6/2010 |
| WO | WO 00/70655 | 11/2000 |
| WO | WO 2004/010736 A1 | 1/2004 |
| WO | WO 2005/019373 A2 | 3/2005 |
| WO | WO 2005/113704 A2 | 12/2005 |
| WO | WO 2006/056418 A2 | 6/2006 |
| WO | WO 2006/067074 A1 | 6/2006 |
| WO | WO 2006/121811 A1 | 11/2006 |
| WO | WO 2006/128800 A1 | 12/2006 |
| WO | WO 2007/077810 A1 | 7/2007 |
| WO | WO 2007/108362 A1 | 9/2007 |
| WO | WO 2007/108459 A1 | 9/2007 |
| WO | WO 2007/114244 A1 | 10/2007 |
| WO | WO 2007/115970 A1 | 10/2007 |
| WO | WO 2007/115981 A1 | 10/2007 |
| WO | WO 2007/119816 A1 | 10/2007 |
| WO | WO 2008/000727 A1 | 1/2008 |
| WO | WO 2008/029652 A1 | 3/2008 |
| WO | WO 2008/029729 A1 | 3/2008 |
| WO | WO 2008/034758 A2 | 3/2008 |
| WO | WO 2008/035571 A1 | 3/2008 |
| WO | WO 2008/072596 A1 | 6/2008 |
| WO | WO 2008/090912 A1 | 7/2008 |
| WO | WO 2008/140114 A1 | 11/2008 |
| WO | WO 2008/146838 A1 | 12/2008 |
| WO | WO 2008/156105 A1 | 12/2008 |
| WO | WO 2009/003898 A1 | 1/2009 |
| WO | WO 2009/003919 A1 | 1/2009 |
| WO | WO 2009/008099 A1 | 1/2009 |
| WO | WO 2009/008100 A1 | 1/2009 |
| WO | WO 2009/021336 A1 | 2/2009 |
| WO | WO 2009/060742 A1 | 5/2009 |
| WO | WO 2009/060757 A1 | 5/2009 |
| WO | WO 2009/060779 A1 | 5/2009 |
| WO | WO 2009/060780 A1 | 5/2009 |
| WO | WO 2009/063757 A1 | 5/2009 |
| WO | WO 2009/084413 A1 | 7/2009 |
| WO | WO 2009/086028 A2 | 7/2009 |
| WO | WO 2009/104488 A1 | 8/2009 |
| WO | WO 2010/001830 A1 | 1/2010 |
| WO | WO 2010/004877 A1 | 1/2010 |
| WO | WO 2010/040777 A1 | 4/2010 |
| WO | WO 2010/044342 A1 | 4/2010 |
| WO | WO 2010/067746 A1 | 6/2010 |
| WO | WO 2010/079051 A1 | 7/2010 |
| WO | WO 2010/079678 A1 | 7/2010 |
| WO | WO 2010/087222 A1 | 8/2010 |
| WO | WO 2010/090077 A1 | 8/2010 |
| WO | WO 2010/095564 A1 | 8/2010 |
| WO | WO 2011/051404 A1 | 5/2011 |

OTHER PUBLICATIONS

International Search Report issued Sep. 8, 2011, in Patent Application No. PCT/IB2011/051647.

U.S. Appl. No. 13/504,725, filed Apr. 27, 2012, Fuchs, et al.

Yabing QI, et al., "Use of a High Electron-Affinity Molybdenum Dithiolene Complex to p-Dope Hole-Transport Layers", J. Am. Chem. Soc., vol. 131, 2009, pp. 12530-12531.

* cited by examiner

BRIDGED BENZIMIDAZOLE-CARBENE COMPLEXES AND USE THEREOF IN OLEDS

The present invention relates to heteroleptic iridium complexes of the formula (I) shown below:

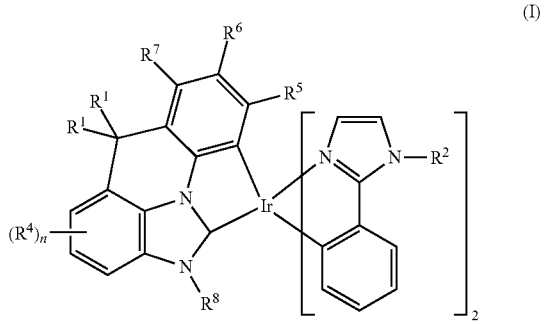

in which $R^5$ and $R^6$ together, or $R^6$ and $R^7$ together, form a unit of the formula:

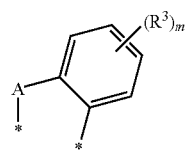

in which * denotes the connection to the carbon atoms of the benzene ring bearing the $R^5$ and $R^6$ radicals or $R^6$ and $R^7$ radicals, the A is connected to the carbon atom bearing the $R^5$, $R^6$ or $R^7$ radical, the $R^1$ to $R^4$ and $R^8$ radicals are each as defined in the description, and A is oxygen or sulfur.

The present invention further comprises light-emitting layers comprising at least one such heteroleptic iridium complex, organic light-emitting diodes (OLEDs) which comprise such heteroleptic iridium complexes, a device selected from the group consisting of illumination elements, stationary visual display units and mobile visual display units, comprising such an OLED, and the use of such a heteroleptic iridium complex in OLEDs, especially as an emitter, matrix material, charge transport material and/or charge blocker.

OLEDs exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are especially suitable for mobile applications, for example for applications in cellphones, laptops, etc. In addition, white OLEDs offer great advantages over the illumination technologies known to date, especially a particularly high efficiency.

Numerous materials, for example including heteroleptic complexes with iridium as the central metal atom, have been proposed in the prior art, which emit light on excitation by electrical current. Among these materials are also those which comprise carbene ligands.

WO 2006/056418 A2 describes, for example, inter alia, heteroleptic metal complexes which comprise N-phenylimidazole or N-phenylbenzimidazole units bonded to the central iridium atom via a carbene bond in the imidazole ring. In the case of the benzimidazole-containing ligands, bridges between the benzene ring of the fusion and the phenyl substituent are also disclosed, as are complexes in which the phenyl substituent is part of a dibenzofuran unit. However, compounds of formula (I) according to the present invention are not to be found in this document.

WO 2006/121811 A1 discloses phosphorescent heteroleptic metal complexes which comprise carbene ligands. The complexes specified in WO 2006/121811 A1, for example iridium complexes, all have benzimidazolocarbenes (benzimidazolylidenes) as carbene ligands. Compounds of the formula (I) cited at the outset are, however, not disclosed in WO 2006/121811 A1.

WO 2006/067074 A1 likewise discloses electroluminescent heteroleptic metal complexes with carbene ligands. The noncarbene ligands used include arylpyridines, arylpyrazoles and aryltriazoles. The use of 2-phenyl-1H-imidazoles as noncarbene ligands is not disclosed in WO 2006/067074 A1.

WO 2007/115981 discloses heteroleptic metal complexes comprising both carbene ligands and heterocyclic noncarbene ligands, a process for preparation thereof and the use of these compounds in OLEDs. However, the compounds disclosed by way of example in WO 2007/115981 do not comprise any combination of ligands according to the present invention.

Even though iridium complexes which exhibit electroluminescence especially in the visible region, more particularly in the red, green and especially blue region, of the electromagnetic spectrum are already known, the provision of further compounds which possess high quantum yields and at the same time especially also exhibit long diode lifetimes is desirable.

In the context of the present invention, electroluminescence is understood to mean both electrofluorescence and electrophosphorescence.

It is therefore an object of the present invention to provide alternative iridium complexes which are suitable for electroluminescence in the visible region, more particularly in the blue, red and green region, of the electromagnetic spectrum, which enables the production of full-color displays and white OLEDs.

It is a further object of the present invention to provide corresponding complexes which can be used as a mixture with a host compound or in substance, i.e. in the absence of host substances, as a light-emitting layer in OLEDs.

It is a further object of the present invention to provide corresponding complexes which have a high quantum yield and a high stability in diodes. The complexes should be usable as an emitter, matrix material, charge transport material or charge blocker in OLEDs.

These objects are achieved in accordance with the invention by a metal-carbene complex of the general formula (I)

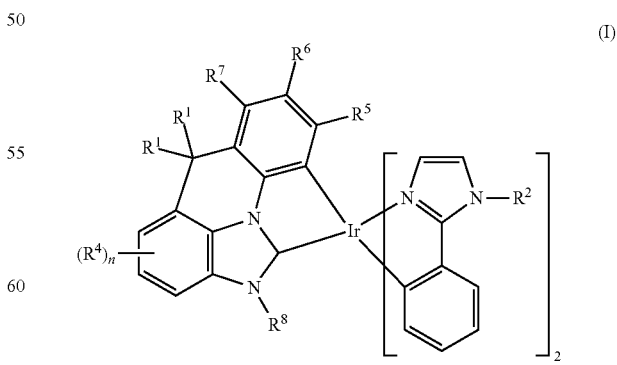

in which the variables are each defined as follows:
$R^1$ is independently hydrogen, a linear or branched alkyl radical which has 1 to 20 carbon atoms, is optionally interrupted by at least one heteroatom and optionally bears at least one functional group, a cycloalkyl radical which has 3 to 20 carbon atoms, is optionally interrupted by at least one heteroatom and optionally bears at least one functional group, a substituted or unsubstituted aryl radical which has 6 to 30 carbon atoms and optionally bears at least one functional group, a substituted or unsubstituted heteroaryl radical which has a total of 5 to 18 carbon atoms and heteroatoms and optionally bears at least one functional group, or the two $R^1$ radicals, together with the carbon atom to which they are bonded, are a substituted or unsubstituted $C_5$, $C_6$, $C_7$ or $C_8$ ring, $R^5$ and $R^6$ together, or $R^6$ and $R^7$ together, form a unit of the formula:

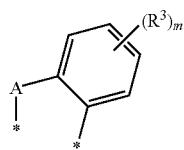

in which * denotes the connection to the carbon atoms of the benzene ring bearing the $R^5$ and $R^6$ radicals or $R^6$ and $R^7$ radicals, and the A is connected to the carbon atom bearing the $R^5$, $R^6$ or $R^7$ radical, A is oxygen or sulfur, $R^2$ is a linear or branched alkyl radical which has 1 to 20 carbon atoms, is optionally interrupted by at least one heteroatom and optionally bears at least one functional group, a cycloalkyl radical which has 3 to 20 carbon atoms, is optionally interrupted by at least one heteroatom and optionally bears at least one functional group, a substituted or unsubstituted aryl radical which has 6 to 30 carbon atoms and optionally bears at least one functional group, a substituted or unsubstituted heteroaryl radical which has a total of 5 to 18 carbon atoms and/or heteroatoms and optionally bears at least one functional group, $R^3$, $R^4$ are each independently a linear or branched alkyl radical which has 1 to 20 carbon atoms, is optionally interrupted by at least one heteroatom and optionally bears at least one functional group, a cycloalkyl radical which has 3 to 20 carbon atoms, is optionally interrupted by at least one heteroatom and optionally bears at least one functional group, a substituted or unsubstituted aryl radical which has 6 to 30 carbon atoms and optionally bears at least one functional group, a substituted or unsubstituted heteroaryl radical which has a total of 5 to 18 carbon atoms and/or heteroatoms and optionally bears at least one functional group, $R^8$ is a linear or branched alkyl radical having 1 to 4 carbon atoms, m, n are each independently 0, 1, 2 or 3.

In the context of the present invention, the terms aryl radical, unit or group, heteroaryl radical, unit or group, alkyl radical, unit or group, and cycloalkyl radical, unit or group are each defined as follows:

An aryl radical or an aryl group is especially understood to mean a radical with a base skeleton of 6 to 30 carbon atoms, preferably 6 to 18 carbon atoms, which is formed from one aromatic ring or a plurality of fused aromatic rings. Suitable base skeletons are, for example, phenyl, benzyl, naphthyl, anthracenyl or phenanthrenyl. This base skeleton may be unsubstituted, which means that all carbon atoms which are substitutable bear hydrogen atoms, or substituted at one, more than one or all substitutable positions of the base skeleton. Suitable substituents are, for example, alkyl radicals, preferably alkyl radicals having 1 to 8 carbon atoms, more preferably methyl, ethyl, i-propyl or t-butyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals, alkenyl radicals, preferably alkenyl radicals which bear a double bond, more preferably alkenyl radicals with one double bond and 1 to 8 carbon atoms, or groups with donor or acceptor action. Groups with donor action are understood to mean groups which have a +I and/or +M effect, and groups with acceptor action are understood to mean groups which have a −I and/or −M effect. Suitable groups with donor or acceptor action are halogen radicals, preferably F, Cl, Br, more preferably F, alkyl radicals, alkoxy radicals, aryloxy radicals, carbonyl radicals, ester radicals, amine radicals, amide radicals, $CH_2F$ groups, $CHF_2$ groups, $CF_3$ groups, CN groups, thio groups or SCN groups. The aryl radicals most preferably bear substituents selected from the group consisting of methyl, ethyl, iso-propyl, n-propyl, n-butyl, iso-butyl, tert-butyl, aryloxy, amine, thio groups and alkoxy, or the aryl radicals are unsubstituted. The aryl radical or the aryl group is preferably a phenyl radical which is optionally substituted by at least one of the aforementioned substituents. The phenyl radical more preferably has none, one, two or three of the aforementioned substituents.

A heteroaryl radical or a heteroaryl group is especially understood to mean a radical which has 5 to 30, preferably 5 to 18, carbon atoms and/or heteroatoms and differs from the aforementioned aryl radicals in that at least one carbon atom in the base skeleton of the aryl radicals is replaced by a heteroatom. Preferred heteroatoms are N, O and S. Most preferably, one or two carbon atoms of the base skeleton of the aryl radicals are replaced by heteroatoms. The base skeleton is especially preferably selected from electron-poor systems such as pyridyl, pyrimidyl, pyrazyl and triazolyl, and five-membered heteroaromatics such as pyrrole, furan, thiophene, imidazole, pyrazole, triazole, oxazole and thiazole. The base skeleton may be substituted at one, more than one or all substitutable positions of the base skeleton. Suitable substituents are the same as have already been mentioned for the aryl groups.

An alkyl radical or an alkyl group is especially understood to mean a radical having 1 to 20 carbon atoms, preferably 1 to 10 carbon atoms, more preferably 1 to 8 carbon atoms. This alkyl radical may be branched or unbranched and optionally be interrupted by one or more heteroatoms, preferably N, O or S. In addition, this alkyl radical may be substituted by one or more of the substituents mentioned for the aryl groups. It is likewise possible that the alkyl radical bears one or more aryl groups. All of the aryl groups listed above are suitable. The alkyl radicals are more preferably selected from the group consisting of methyl, ethyl, i-propyl, n-propyl, i-butyl, n-butyl, t-butyl, sec-butyl, i-pentyl, n-pentyl, sec-pentyl, neopentyl, n-hexyl, i-hexyl and sec-hexyl. Very particular preference is given to methyl, i-propyl, tert-butyl.

A cycloalkyl radical or a cycloalkyl group is especially understood to mean a cyclic radical having 3 to 20 carbon atoms, preferably 3 to 10 carbon atoms, more preferably 3 to 8 carbon atoms. This cycloalkyl radical may optionally be interrupted by one or more heteroatoms, preferably N, O or S. In addition, this cycloalkyl radical may be unsubstituted or substituted, i.e. substituted by one or more of the substituents mentioned for the aryl groups. It is likewise possible that the cycloalkyl radical bears one or more aryl groups. All of the aryl groups listed above are suitable.

In the case of the two $R^1$ radicals, these may be different from one another. However, the two $R^1$ radicals are preferably the same.

When the two $R^1$ radicals, together with the carbon atom to which they are bonded, form a substituted $C_5$, $C_6$, $C_7$ or $C_8$ ring, preferably a $C_5$ or $C_6$ ring, useful substituents, as also in the case of the cycloalkyl radical or of the cycloalkyl group, include one or more substituents mentioned for the aryl groups, and one or more aryl groups.

According to the invention, the statements made for the aryl, heteroaryl, alkyl and cycloalkyl radicals apply independently to the $R^1$, $R^2$, $R^3$ and $R^4$ radicals.

In a preferred embodiment, the variables $R^1$, $R^2$, $R^3$, $R^4$ and $R^8$ in the metal-carbene complexes of the formula (I) are each defined as follows:

$R^1$ is independently a linear or branched alkyl radical having 1 to 10 carbon atoms, a substituted or unsubstituted aryl radical having 6 to 30 carbon atoms, or the two $R^1$ radicals, together with the carbon atom to which they are bonded, form a substituted or unsubstituted $C_5$ or $C_6$ ring, $R^2$ is an ortho,ortho'-disubstituted aryl radical having 6 to 30 carbon atoms, $R^3$, $R^4$ are each a linear or branched alkyl radical having 1 to 10 carbon atoms, $R^8$ is a linear or branched alkyl radical having 1 to 4 carbon atoms, m, n are each independently 0, 1 or 2.

Linear or branched alkyl radicals having 1 to 10 carbon atoms for $R^1$, $R^2$, $R^3$ and $R^4$ are independently methyl, ethyl, propyl, isopropyl, butyl, tert-butyl and pentyl.

Linear or branched alkyl radicals having 1 to 4 carbon atoms for $R^8$ are independently methyl, ethyl, propyl, isopropyl, butyl and tert-butyl. $R^8$ is more preferably methyl.

Substituted or unsubstituted aryl radicals having 6 to 30 carbon atoms for $R^1$ and $R^2$ are independently unsubstituted phenyl or substituted phenyl, preferably ortho-substituted, for example by alkyl radicals having 1 to 6 carbon atoms, for instance methyl, ethyl or propyl, especially isopropyl.

In a particularly preferred embodiment, the variables $R^1$, $R^2$, $R^3$, $R^4$ and $R^8$ in the metal-carbene complexes of the formula (I) are each defined as follows:

$R^1$ is a linear or branched alkyl radical having 1 to 4 carbon atoms, $R^2$ is an ortho,ortho'-dialkylated phenyl radical, $R^3$, $R^4$ are each a linear or branched alkyl radical having 1 to 4 carbon atoms, $R^8$ is a linear or branched alkyl radical having 1 to 4 carbon atoms, and m, n are each independently 0, 1 or 2.

Linear or branched alkyl radicals having 1 to 4 carbon atoms for $R^1$, $R^2$, $R^3$, $R^4$ and $R^8$ are independently methyl, ethyl, propyl, isopropyl, butyl and tert-butyl. Options for $R^8$ are methyl, ethyl, propyl, isopropyl, butyl and tert-butyl. $R^8$ is more preferably methyl.

The ortho,ortho'-dialkylated phenyl radical in the definition of $R^2$ is preferably substituted by alkyl radicals having 1 to 6 carbon atoms, for instance methyl, ethyl or propyl, especially by isopropyl. The two ortho,ortho'-substituents may be different from one another. However, they are preferably the same.

In the general and the preferred embodiment of the inventive complexes, $R^5$ and $R^6$ together, or $R^6$ and $R^7$ together, form a unit of the formula:

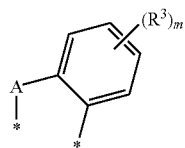

in which * denotes the connection to the carbon atoms of the benzene ring bearing the $R^5$ and $R^6$ or $R^6$ and $R^7$ radicals, and the A is connected to the carbon atom bearing the $R^5$, $R^6$ or $R^7$ radical. A here is oxygen or sulfur.

In the particularly preferred embodiment, $R^6$ and $R^7$ together form a unit of the formula:

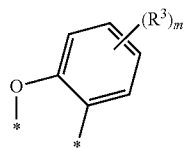

in which * denotes the connection to the carbon atoms of the benzene ring bearing the $R^6$ and $R^7$ radicals, and the oxygen atom is connected to the carbon atom bearing the $R^7$ radical.

In the case that m and n assume values of 2 or 3, the corresponding substituents may be the same or different.

In the general case and in the preferred embodiment, the following isomeric structures (I-1) to (I-4) arise for the inventive metal-carbene complexes of the formula (I):

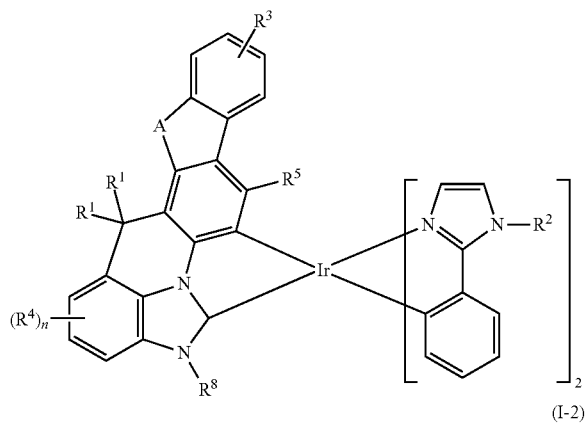

(I-1)

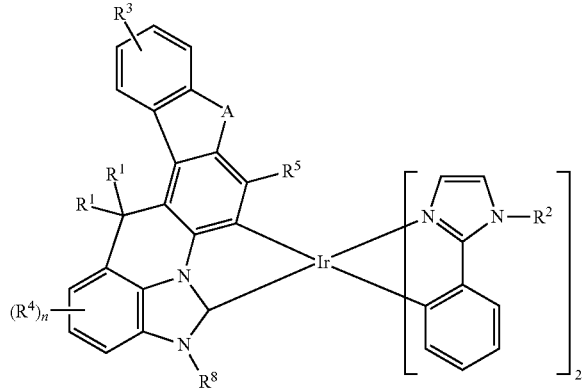

(I-2)

(I-3)

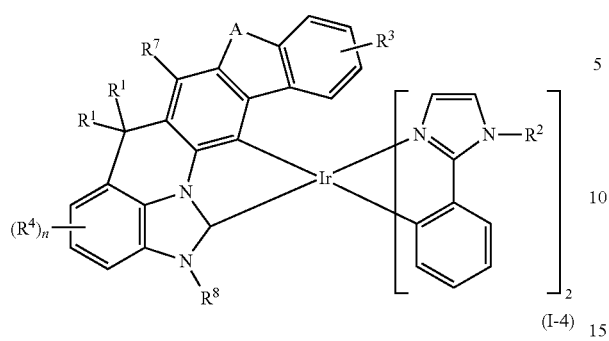

(I-4)

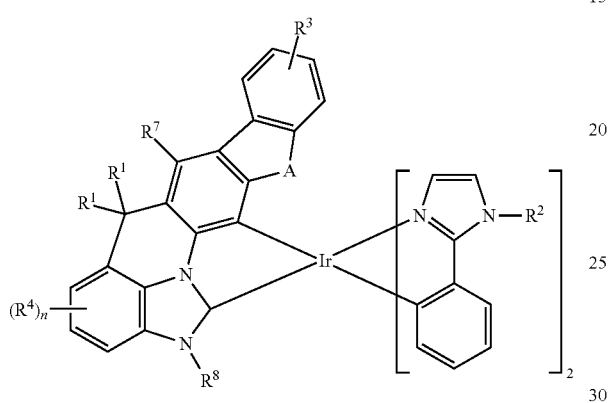

The structure of the inventive metal-carbene complexes of the formula (I) in the particularly preferred embodiment is shown in (I-5):

(I-5)

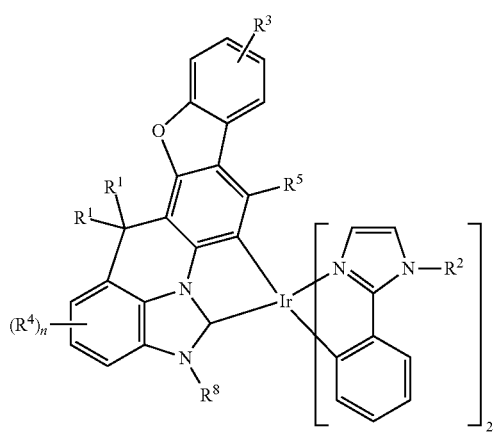

Furthermore, the following isomers S1 to S4 are possible for the metal-carbene complexes of the formulae (I-1) to (I-5), each of which may be present in the form of two enantiomers (a and b):

S1a

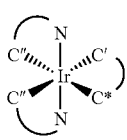

S2a

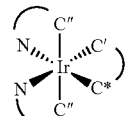

S3a

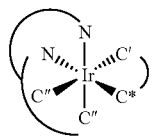

S4a

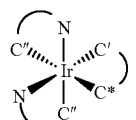

S1b

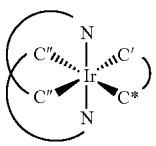

S2b

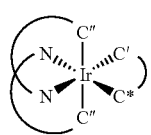

S3b

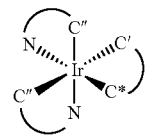

S4b

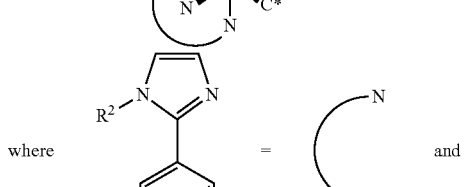

where 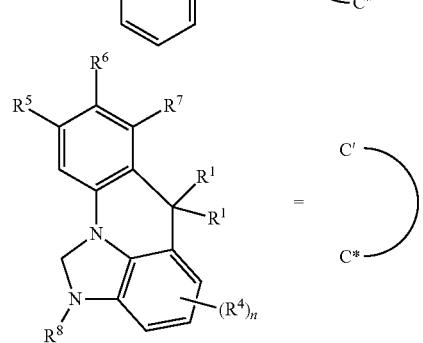

In the present application, owing to the arrangement of the two 2-phenyl-1H-imidazole ligands, the isomers S1a/S1b and S2a/S2b are designated as pseudo-meridional (pseudo-mer) isomers, and the isomers S3a/S3b and S4a/S4b as pseudo-facial (pseudo-fac) isomers.

It has been found that, surprisingly, the isomers S3 and S4 when used in OLEDs give particularly good results with regard to efficiency and lifetime. Therefore, particular preference is given in accordance with the invention to the isomers S3a/S3b and S4a/S4b, i.e. the pseudo-facial isomers.

In general, the different isomers of the inventive metal-carbene complexes (I) can be separated by processes known to those skilled in the art, for example by chromatography, sublimation or crystallization. The different isomers can generally be interconverted thermally or photochemically, by means of suitable reaction conditions (for example pH).

The present invention relates both to the particular isomers or enantiomers of the heteroleptic complexes of the formula (I) and to mixtures of different isomers or enantiomers in any mixing ratio.

The following are listed by way of example hereinafter as inventive metal-carbene complexes:

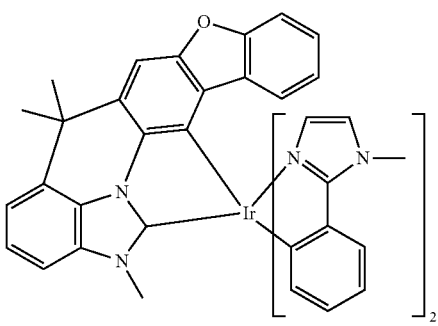

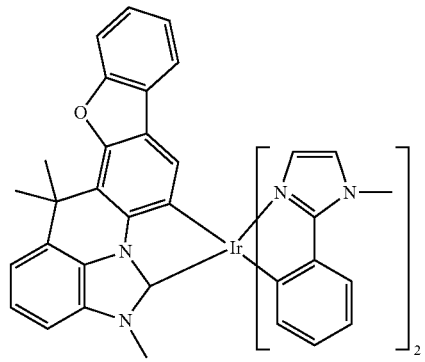

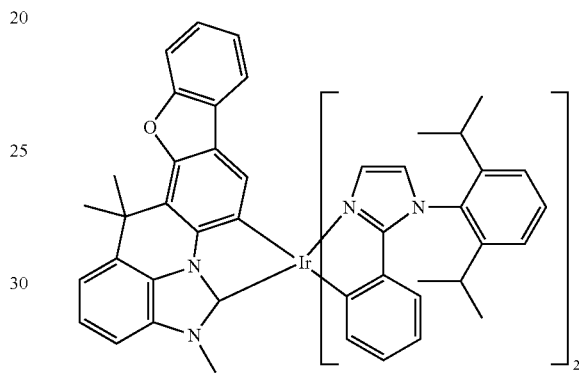

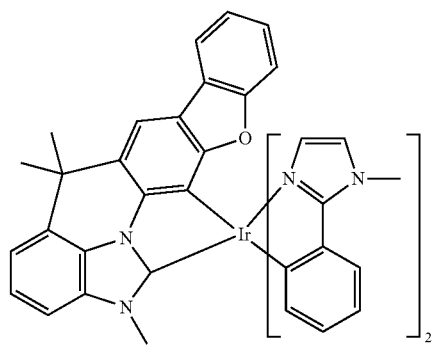

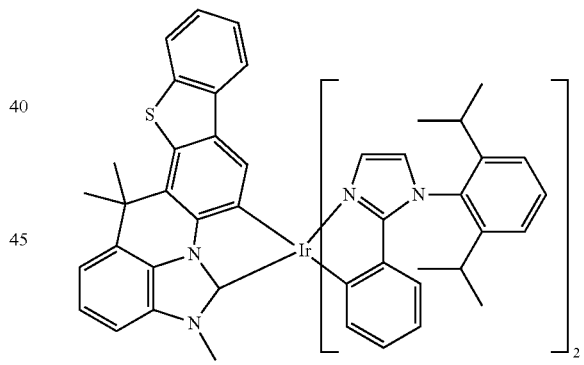

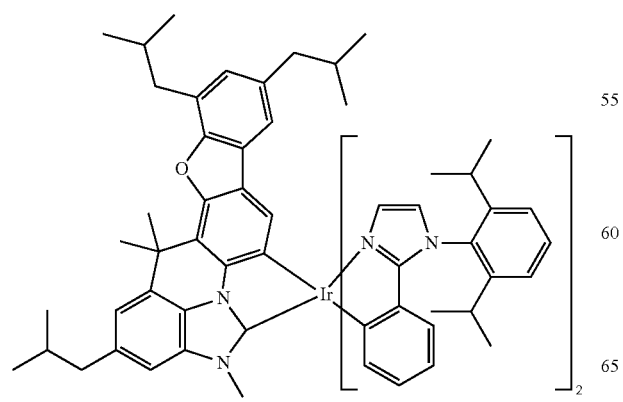

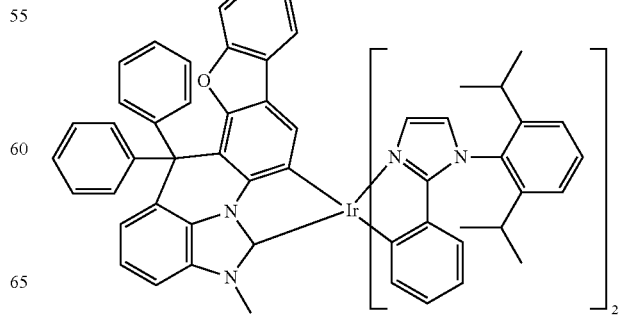

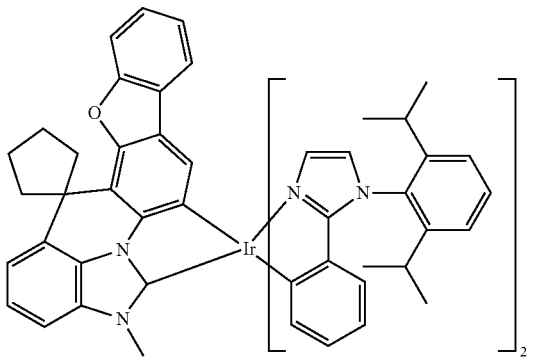
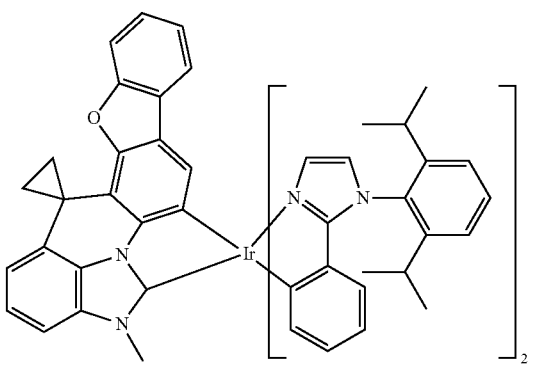
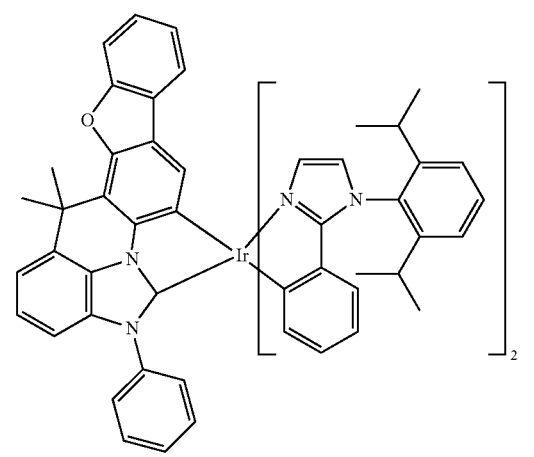
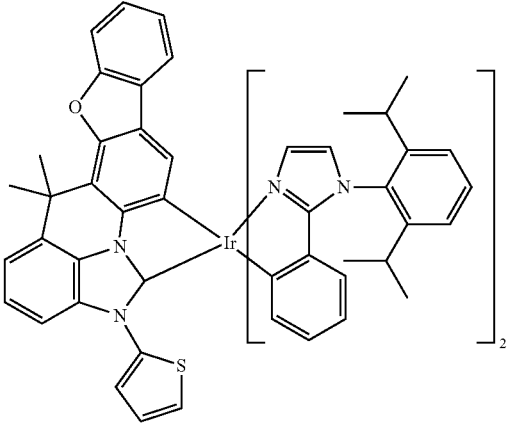
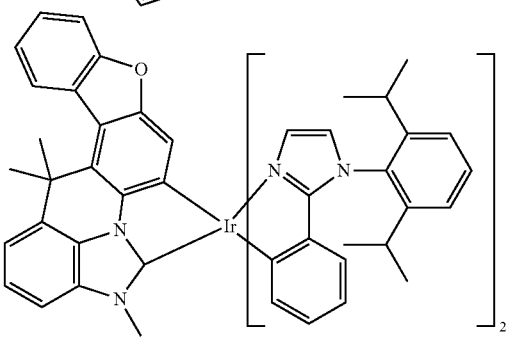

The inventive metal-carbene complexes of the formula (I) can be obtained by:

contacting at least one precursor compound comprising the iridium and the ligand which is connected to the iridium via noncarbene bonds in the complexes of the general formula (I), and then reacting the intermediate obtained with the ligand which is connected to the iridium via a carbene bond in the complexes of the general formula (I), or ligand precursor thereof, for example a corresponding benzimidazolium salt, or contacting at least one precursor compound comprising the iridium and a ligand which is bonded to M via a carbene bond in the complexes of the general formula (I), and then reacting the resulting intermediate with the ligand which is connected to the iridium via noncarbene bonds in the complexes of the general formula (I).

Preference is given to reacting a complex comprising corresponding noncarbene ligands connected to the iridium with corresponding carbene ligands, preferably in deprotonated form as the free carbene or in the form of a protected carbene, for example as the silver-carbene complex. The precursor compounds used comprise the corresponding substituents $R^1$ to $R^8$ present in the complexes of the general formula (I).

Complexes comprising corresponding noncarbene ligands connected to the iridium are known to those skilled in the art. In addition to the noncarbene ligands present in the complex of the general formula (I), these complexes used as precursor compounds may comprise further ligands known to those skilled in the art, for example halides, especially chloride. Further suitable ligands are, for example, 1,5-cyclooctadiene (COD), phosphines, cyanides, alkoxides, pseudohalides and/or alkyl.

Advantageous complexes which comprise the corresponding noncarbene ligands connected to the iridium are, for example compounds of the general formula (III)

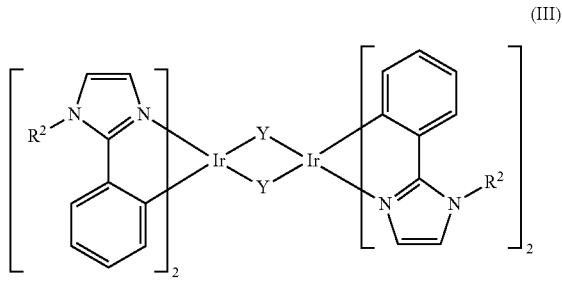

(III)

with the above definitions for $R^2$, where Y may independently be F, Cl, Br, I, methoxy or carboxylate.

Particularly preferred precursor compounds for the carbene ligands used in complexes of the general formula (I) correspond, for example, to the general formula (IV-a) or (IV-b)

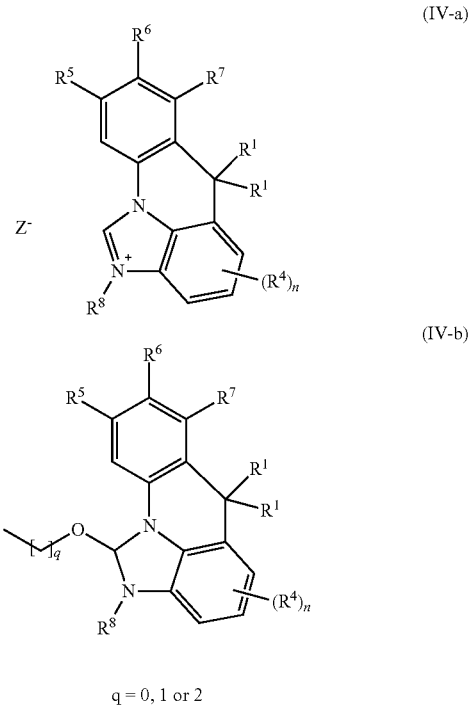

q = 0, 1 or 2 with the above definitions for $R^1$, $R^4$, $R^5$, $R^6$, $R^7$ and $R^8$, where Z is defined as F, Cl, Br, I, $BF_4$, $PF_6$, $ClO_4$ or $SbF_6$.

The carbene ligand precursors are deprotonated, preferably before the reaction, for example, by basic compounds known to those skilled in the art, for example basic metalates, basic metal acetates, acetylacetonates or alkoxides, or bases such as KO$^t$Bu, NaO$^t$Bu, LiO$^t$Bu, NaH, silylamides, $Ag_2O$ and phosphazene bases. In addition, the carbene can also be released by removing volatile substances, for example lower alcohols such as methanol or ethanol, for example at elevated temperature and/or reduced pressure, from precursor compounds of the carbene ligands. Corresponding processes are known to those skilled in the art.

The contacting is preferably effected in a solvent. Suitable solvents are known to those skilled in the art and are preferably selected from the group consisting of aromatic or aliphatic solvents, for example benzene or toluene, cyclic or acyclic ethers, alcohols, esters, amides, ketones, nitriles, halogenated compounds and mixtures thereof. Particularly preferred solvents are toluene, xylenes, mesitylene, dioxane and THF.

The molar ratio of metal-noncarbene complex used to carbene ligand precursor used is generally 1:10 to 10:1, preferably 1:1 to 1:5, more preferably 1:2 to 1:4.

The contacting is generally effected at a temperature of 20 to 200° C., preferably 50 to 150° C., more preferably 60 to 130° C.

The reaction time depends on the desired carbene complex and is generally 0.02 to 50 hours, preferably 0.1 to 24 hours, more preferably 1 to 12 hours.

The complexes of the general formula (I) obtained after the reaction can optionally be purified by processes known to those skilled in the art, for example washing, crystallization or chromatography, and optionally isomerized under conditions likewise known to those skilled in the art, for example thermally or photochemically.

The inventive heteroleptic complexes and mixtures thereof are outstandingly suitable as emitter molecules in OLEDs. Variations in the ligands make it possible to provide corresponding complexes which exhibit electroluminescence in the red, green and especially in the blue region of the electromagnetic spectrum. The inventive heteroleptic complexes of the general formula (I) are therefore outstandingly suitable as emitter substances, since they have emission (electroluminescence) in the visible region of the electromagnetic spectrum, for example at 400 to 600 nm. The inventive heteroleptic complexes make it possible to provide compounds which have electroluminescence in the red, green and especially in the blue region of the electromagnetic spectrum. It is thus possible, with the aid of the inventive heteroleptic complexes as emitter substances, to provide industrially usable OLEDs.

In the case of the inventive heteroleptic complexes of the general formula (I), the particularly good efficiencies and lifetimes thereof when used in OLEDs should be emphasized.

The present application further also provides for the use of the heteroleptic complexes of the general formula (I) in OLEDs, preferably as an emitter, matrix material, charge transport material and/or charge blocker.

Organic light-emitting diodes are in principle formed from a plurality of layers:

anode (1)
hole-transporting layer (2)
light-emitting layer (3)
electron-transporting layer (4)
cathode (5)

The heteroleptic complexes of the general formula (I) are preferably used as emitter molecules in the light-emitting layer (3).

The present application therefore further provides a light-emitting layer which comprises at least one inventive metal-carbene complex of the general formula (I) and preferred embodiments thereof. It preferably assumes the function of an emitter molecule. Preferred heteroleptic complexes of the general formula (I) have already been specified above.

The heteroleptic complexes of the general formula (I) used in accordance with the invention may be present in the light-emitting layer in substance, i.e. without further additions. However, it is also possible that, in addition to the heteroleptic complexes of the general formula (I) used in accordance with the invention, further compounds are present in the light-emitting layer. For example, a fluorescent dye may be present in order to alter the emission color of the heteroleptic complex used as the emitter molecule. In addition, a diluent material may be used. This diluent material may be a polymer, for example poly(N-vinylcarbazole) or polysilane. The diluent material may, however, likewise be a small molecule, for example 4,4'-N,N'-dicarbazolebiphenyl (CDP) or tertiary aromatic amines. When a diluent material is used, the proportion of the heteroleptic complexes used in accordance with the invention in the light-emitting layer is generally less than 40% by weight, preferably 3 to 30% by weight. The inventive heteroleptic complexes of the general formula (I) are preferably used in a matrix. The light-emitting layer thus preferably comprises at least one inventive heteroleptic complex of the general formula (I) and a matrix material as diluent material.

Suitable matrix materials are—beside the diluents materials mentioned before—in principle the materials mentioned below as hole and electron transport materials as well as carbene complexes, e.g. the carbene complexes of formula (I) or the carbene complexes mentioned in WO 2005/019373. Especially suitable are carbazole derivatives, e.g. 4,4'-bis(carbazole-9-yl)-2,2'-dimethyl-biphenyl (CDBP), 4,4'-bis(carbazole-9-yl)-biphenyl (CBP), 1,3-bis(N-carbazolyl)benzene (mCP), as well as the matrix materials mentioned in the following applications: WO2008/034758, WO2009/003919.

Further suitable matrix materials are mentioned in the following publications, wherein the matrix materials may be small molecules or (co)polymers of the small molecules mentioned:

WO2007108459 (H-1 to H-37), preferably H-20 to H-22 and H-32 to H-37, more preferably H-20, H-32, H-36, H-37, WO2008035571 A1 (Host 1 to Host 6), JP2010135467 (compounds 1 to 46 and Host-1 to Host-39 and Host-43), WO2009008100 (compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67), WO2009008099 (compounds No. 1 to No. 110), WO2008140114 (compounds 1-1 to 1-50), WO2008090912 (compounds OC-7 to OC-36 and the polymers of Mo-42 to Mo-51), JP2008084913 (H-1 to H-70), WO2007077810 (compounds 1 to 44, preferably 1, 2, 4-6, 8, 19-22, 26, 28-30, 32, 36, 39-44), WO201001830 (the polymers of monomers 1-1 to 1-9, preferably of 1-3, 1-7, and 1-9), WO2008029729 (the (polymers of) compounds 1-1 to 1-36), WO20100443342 (HS-1 to HS-101 and BH-1 to BH-17, preferably BH-1 to BH-17), JP2009182298 (the (co)polymers based on the monomers 1 to 75), JP2009170764, JP2009135183 (the (co)polymers based on the monomers 1-14), WO2009063757 (preferably the (co)polymers based on the monomers 1-1 to 1-26), WO2008146838 (the compounds a-1 to a-43 and 1-1 to 1-46), JP2008207520 (the (co)polymers based on the monomers 1-1 to 1-26), JP2008066569 (the (co)polymers based on the monomers 1-1 to 1-16), WO2008029652 (the (co)polymers based on the monomers 1-1 to 1-52), WO2007114244 (the (co)polymers based on the monomers 1-1 to 1-18), JP2010040830 (the compounds HA-1 to HA-20, HB-1 to HB-16, HC-1 to HC-23 and the (co)polymers based on the monomers HD-1 to HD-12), JP2009021336, WO2010090077 (the compounds 1 to 55), WO2010079678 The compounds H1 to H42), WO2010067746, WO2010044342 (the compounds HS-1 bis HS-101 and Poly-1 to Poly-4), JP2010114180 (the compounds PH-1 to PH-36), US2009284138 (the compounds 1 to 111 and H1 to H71), WO2008072596 (the compounds 1 to 45), JP2010021336 (the compounds H-1 to H-38, preferably H-1), WO2010004877 (the compounds H-1 to H-60), JP2009267255 (the compounds 1-1 to 1-105), WO2009104488 (the compounds 1-1 to 1-38), WO2009086028, US2009153034, US2009134784, WO2009084413 (the compounds 2-1 to 2-56), JP2009114369 (the compounds 2-1 to 2-40), JP2009114370 (the compounds 1 to 67), WO2009060742 (the compounds 2-1 to 2-56), WO2009060757 (the compounds 1-1 to 1-76), WO2009060780 (the compounds 1-1 to 1-70), WO2009060779 (the compounds 1-1 to 1-42), WO2008156105 (the compounds 1 to 54), JP2009059767 (the compounds 1 to 20), JP2008074939 (the compounds 1 to 256), JP2008021687 (the compounds 1 to 50), WO2007119816 (the compounds 1 to 37), WO2010087222 (the compounds H-1 to H-31), WO2010095564 (the compounds HOST-1 to HOST-61), WO2007108362, WO2009003898, WO2009003919, WO2010040777, US2007224446 and WO06128800.

In a particularly preferred embodiment one or more compounds of one or more of the following formulae (V) and/or (VI) are used as matrix material. Preferred embodiments of compounds of the general formulae (V) and (VI) are also mentioned below.

The individual layers among the aforementioned layers of the OLED may in turn be formed from two or more layers. For example, the hole-transporting layer may be formed from one layer, into which holes are injected from the electrode, and a layer which transports the holes away from the hole-injecting layer into the light-emitting layer. The electron-transporting layer may likewise consist of a plurality of layers, for example of a layer in which electrons are injected through the electrode, and a layer which receives electrons from the electron-injecting layer and transports them into the light-emitting layer. These layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is matched optimally to the heteroleptic complexes according to the present invention used as emitter substances in accordance with the invention.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer should be aligned to the work function of the cathode.

The present application further provides an OLED comprising at least one inventive light-emitting layer. The further layers in the OLED may be formed from any material which is typically used in such layers and is known to those skilled in the art.

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole transport materials for layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole transport material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)-cyclobutane (DCZB), N,N,N',N'-tetrakis(4-methylphenyl)-(1,1'-biphenyl)-4,4'-diamine (TTB) and porphyrin compounds such as copper phthalocyanines. Customarily used hole-transporting polymers are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition, it is possible to use carbene complexes as hole conductor materials, in which case the band gap of the at least one hole conductor material is generally greater than the band gap of the emitter material used. In the context of the present invention, band gap is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is Ir(DPBIC)$_3$ with the formula:

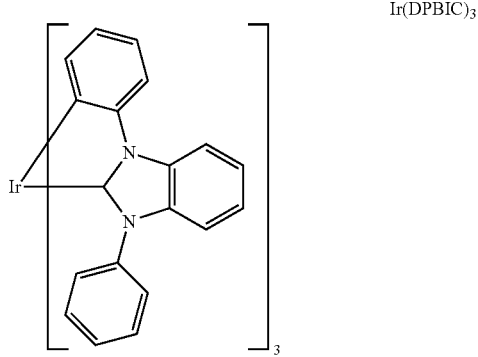

Ir(DPBIC)$_3$

It is likewise possible to use mixtures in the hole-transporting layer, in particular mixtures which lead to electrical p-doping of the hole-transporting layer. p-Doping is achieved by the addition of oxidizing materials. These mixtures may, for example, be mixtures of the abovementioned hole transport materials with MoO$_2$, MoO$_3$, WO$_x$, ReO$_3$, V$_2$O$_5$, 7,7,8,8-tetracyanoquinodimethane (TCNQ), 2,3,5,6-tetrafluoro-7,7,8,8-tetracyanoquinodimethane (F$_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquinodimethane, 2,5-difluoro-7,7,8,8-tetracyanoquinodimethane, dicyanomethylene-1,3,4,5,7,8-hexafluoro-6H-naphthalen-2-ylidene)malononitrile (F$_6$-TNAP), Mo(tfd)$_3$ (from Kahn et al., J. Am. Chem. Soc. 2009, 131 (35), 12530-12531), and with quinone compounds as mentioned in EP 09153776.1.

Suitable electron-transporting materials for layer (4) of the inventive OLEDs comprise metals chelated with oxinoid compounds, such as tris(8-hydroxyquinolato)aluminum (Alq$_3$), compounds based on phenanthroline such as 2,9-dimethyl-4,7-diphenyl-1,10-phenanthroline (DDPA=BCP), 4,7-diphenyl-1,10-phenanthroline (Bphen), 4,7-diphenyl-1,10-phenanthroline (DPA) or phenanthroline derivatives disclosed in EP1786050 or in EP1097981, and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer (4) may serve both to ease the electron transport and as a buffer layer or as a barrier layer in order to prevent quenching of the exciton at the interfaces of the layers of the OLED. Layer (4) preferably improves the mobility of the electrons and reduces quenching of the exciton.

It is likewise possible to use mixtures of at least two materials in the electron-transporting layer, in which case at least one material is electron-conducting. Preferably, in such mixed electron-transporting layers, at least one phenanthroline compound is used. More preferably, in mixed electron-transporting layers, in addition to at least one phenanthroline compound, alkali metal hydroxyquinolate complexes, for example Liq, are used. In addition, it is possible to use mixtures which lead to electrical n-doping of the electron-transporting layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, Cs$_2$CO$_3$, with alkali metal complexes, for example 8-hydroxyquinolatolithium (Liq), and with Y, Ce, Sm, Gd, Tb, Er, Tm, Yb, Li$_3$N, Rb$_2$CO$_3$, dipotassium phthalate, W(hpp)$_4$ from EP 1786050, or with compounds as described in EP1837926 B1.

The inventive OLED may comprise an electron-transporting layer which consists of at least two different materials, of which at least one material should be electron-conducting.

In a preferred embodiment, the inventive OLED comprises, in the electron-transporting layer, at least one phenanthroline derivative.

In a further preferred embodiment, the inventive OLED comprises, in the electron-transporting layer, at least one phenanthroline derivative and at least one alkali metal hydroxyquinolate complex.

In a further preferred embodiment, the OLED comprises, in the electron-transporting layer, at least one phenanthroline derivative and 8-hydroxyquinolatolithium.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds such as 8-hydroxyquinolatolithium (Liq) or LiF may be applied between the organic layer and the cathode as an electron injection layer in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:

a hole injection layer between the anode (1) and the hole-transporting layer (2);

a blocking layer for electrons between the hole-transporting layer (2) and the light-emitting layer (3);

a blocking layer for holes between the light-emitting layer (3) and the electron-transporting layer (4);

an electron injection layer between the electron-transporting layer (4) and the cathode (5).

Those skilled in the art know how suitable materials have to be selected (for example on the basis of electrochemical investigations). Suitable materials for the individual layers are known to those skilled in the art and disclosed, for example, in WO 00/70655.

In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass or polymer films. For the vapor deposition, customary techniques may be used, such as thermal evaporation, chemical vapor deposition and others. In an alternative process, the organic layers may be coated from solutions or dispersions in suitable solvents, in which case coating techniques known to those skilled in the art are employed.

In general, the different layers have the following thicknesses: anode (2) 500 to 5000 Å (ångström), preferably 1000 to 2000 Å; hole-transporting layer (3) 50 to 1000 Å, preferably 200 to 800 Å; light-emitting layer (4) 10 to 1000 Å, preferably 100 to 800 Å; electron-transporting layer (5) 50 to 1000 Å, preferably 200 to 800 Å; cathode (6) 200 to 10 000 Å, preferably 300 to 5000 Å. The position of the recombination zone of holes and electrons in the inventive OLED and thus the emission spectrum of the OLED may be influenced by the relative thickness of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

In a preferred embodiment, the present invention relates to an OLED comprising at least one inventive heteroleptic complex of the general formula (I), and at least one compound of the formula (V)

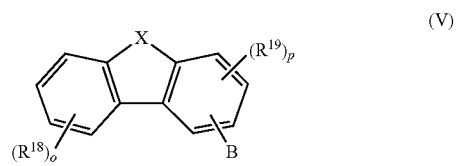

in which

X is NR, S, O or PR, preferably S or O, more preferably O;

R is aryl, heteroaryl, alkyl, cycloalkyl or heterocycloalkyl;

B is $-NR^{20}R^{21}$, $-P(O)R^{22}R^{23}$, $-PR^{24}R^{25}$, $-S(O)_2R^{26}$, $-S(O)R^{27}$, $-SR^{28}$ or $-OR^{29}$, preferably $-NR^{20}R^{21}$; more preferably

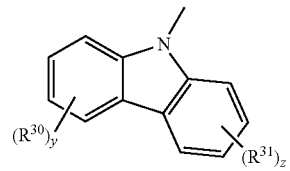

in which $R^{30}$, $R^{31}$ are each independently alkyl, cycloalkyl, heterocycloalkyl, aryl or heteroaryl; preferably methyl, carbazolyl, dibenzofuryl or dibenzothienyl;

y, z are each independently 0, 1, 2, 3 or 4, preferably 0 or 1;

$R^{18}$, $R^{19}$ are each independently alkyl, cycloalkyl, heterocycloalkyl, aryl, heteroaryl, $SiR^{15}R^{16}R^{17}$, a group B or a group with donor or acceptor action;

o is 0, 1, 2, 3 or 4;

p is 0, 1, 2 or 3;

$R^{20}$, $R^{21}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;

$R^{15}$, $R^{16}$, $R^{17}$, $R^{22}$, $R^{23}$, $R^{24}$, $R^{25}$, $R^{26}$, $R^{27}$, $R^{28}$, $R^{29}$ are each independently aryl, heteroaryl, alkyl, cycloalkyl or heterocycloalkyl, or two units oft the general formula (V) are linked via a linear or branched, saturated or unsaturated bridge, which is optionally interrupted by at least one hetero atom, via a bond or via O.

Preferred are compounds of formula (V) in which:

X is S or O, preferably O, and

B is

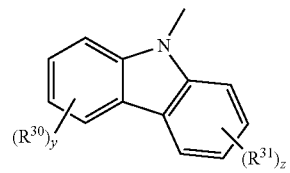

in which

R$^{30}$, R$^{31}$ are each independently alkyl, cycloalkyl, heterocycloalkyl, aryl or heteroaryl; preferably methyl, carbazolyl, dibenzofuryl or dibenzothienyl;

y, z are each independently 0, 1, 2, 3 or 4, preferably 0 or 1.

More preferred compounds of formula (V) show the following formula (Va):

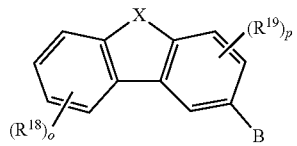

(Va)

in which the symbols and indices B, X, R$^{18}$, R$^{19}$, o and p have the meanings mentioned before.

Even more preferred compounds of formula (V) show the following formula (Vaa):

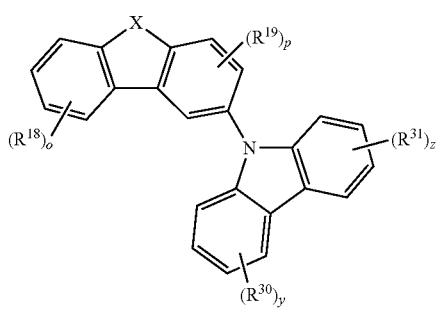

(Vaa)

in which the symbols and indices R$^{30}$, R$^{31}$ y, z, X, R$^{18}$, R$^{19}$, o and p have the meanings mentioned before.

In a particularly preferred embodiment the symbols and indices in formula (Vaa) have the following meanings:

X is O or S, preferably O;

o is 1;

p is 0;

y, z are each independently 0 or 1; and

R$^{30}$, R$^{31}$ are each independently methyl, carbazolyl, dibenzofuryl or dibenzothienyl R$^{18}$ is substituted phenyl, carbazolyl, dibenzofuryl or dibenzothienyl.

In a further preferred embodiment the compounds of formula (V) show the formula (II) oder (II*):

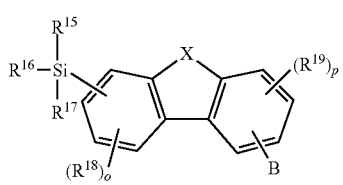

(II)

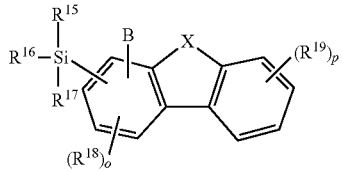

(II*)

in which X, B, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$ and R$^{29}$, o and p are each defined as follows:

X is NR, S, O or PR where R is aryl, heteroaryl, alkyl, cycloalkyl or heterocycloalkyl each having a total of 1 to 30 carbon atoms and/or heteroatoms, B is —NR$^{20}$R$^{21}$, —P(O)R$^{22}$R$^{23}$, —PR$^{24}$R$^{25}$, —S(O)$_2$R$^{26}$, —S(O)R$^{27}$, —SR$^{28}$ or —OR$^{29}$,

R$^{22}$, R$^{23}$,

R$^{24}$, R$^{28}$,

R$^{26}$, R$^{27}$,

R$^{28}$ and

R$^{29}$ are each independently aryl, heteroaryl, alkyl, cycloalkyl or heterocycloalkyl each having a total of 1 to 40 carbon atoms and/or heteroatoms,

R$^{15}$, R$^{16}$,

R$^{17}$ are each independently aryl, heteroaryl, alkyl, cycloalkyl or heterocycloalkyl each having a total of 1 to 20 carbon atoms and/or heteroatoms, where at least one of the R$^{15}$, R$^{16}$ and R$^{17}$ radicals is aryl or heteroaryl, preferably independently aryl or alkyl each having a total of 1 to 10 carbon atoms and/or heteroatoms, where at least one of the R$^{15}$, R$^{16}$ and R$^{17}$ radicals is aryl, R$^{18}$, R$^{19}$ are each independently alkyl, cycloalkyl, heterocycloalkyl, aryl, heteroaryl each having a total of 1 to 20 carbon atoms and/or heteroatoms and/or a B group and/or a group with donor or acceptor action, o, p are each independently 0, 1, 2 or 3, R$^{20}$, R$^{21}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action.

In a further embodiment two units oft the general formula (II) and/or (II*) are linked via a linear or branched, saturated or unsaturated bridge, which is optionally interrupted by at least one hetero atom, via a bond or via O, wherein said bridge is linked to the Si atoms instead of R$^{16}$ in the general formulae (II) and/or (II*).

The compounds of the general formula (V) can be used as a matrix (diluent material), hole/exciton blocker, electron/exciton blocker, electron transport material or hole transport material in combination with the heteroleptic complexes claimed, which then serve as emitters. Inventive OLEDs which include both at least one compound of the formula (V) and a compound of the formula (I) exhibit particularly good efficiencies and lifetimes. Depending on the function in which the compound of the formula (V) is used, it is present in pure form or in different mixing ratios. In a particularly preferred embodiment one or more compounds of formula (V) are used as matrix material in the light emitting layer and/or as hole/exciton blockers.

The compounds of the general formula (II) can be preferably used as a matrix (diluent material), hole blocker, exciton blocker, electron transport material or hole transport material in combination with the heteroleptic complexes claimed, which then serve as emitters. Inventive OLEDs which include both at least one compound of the formula (II) and a compound of the formula (I) exhibit particularly good efficiencies and lifetimes. Depending on the function in which the compound of the formula (II) is used, it is present in pure form or in different mixing ratios.

Concerning the compounds of the general formula (V), especially the residues $R^{18}$ to $R^{77}$, as well as concerning the compounds of formula (VI) mentioned below the following applies:

The terms aryl radical, unit or group, heteroaryl radical, unit or group, alkyl radical, unit or group, cycloalkyl radical, unit or group have been already defined before. In the context of the present invention, the terms heterocycloalkyl radical, unit or group, alkenyl radical, unit or group, alkinyl radical, unit or group p, and groups with donor and/or acceptor action are each defined as follows:

A heterocycloalkyl radical or a heterocycloalkyl group is especially understood to mean a radical which differs from the cycloalkyl radicals mentioned before in the feature that at least one carbon atom in the skeletal structure of the cycloalkyl radical is replaced by a heteroatom. Preferred heteroatoms are N, O and S. More preferably, one or two carbon atoms in the skeletal structure of the cycloalkyl radical are replaced by heteroatoms. Examples for suitable heterocycloalkyl radicals are radicals derived from pyrrolidine, piperidine, piperazine, tetrahydrofurane, dioxane.

An alkenyl radical or an alkenyl group is especially understood to mean a radical corresponding to the alkyl radicals mentioned before, having at least two carbon atoms, with the difference that at least one C—C single bond in the alkyl radical ist replaced by a C=C double bond. Preferably, the alkenyl radical comprises one or two double bonds.

An alkinyl radical or an alkinyl group is especially understood to mean a radical corresponding to the alkyl radicals mentioned before, having at least two carbon atoms, with the difference that at least one C—C single bond in the alkyl radical ist replaced by a C≡C triple bond. Preferably, the alkinyl radical comprises one or two triple bonds.

A group with donor action or a group with acceptor action is understood to mean the following:

Groups with donor action are understood to mean groups which have a +I and/or +M effect, and groups with acceptor action are understood to mean groups which have a −I and/or −M effect. Preferred suitable groups are selected from $C_1$-$C_{20}$-alkoxy, $C_6$-$C_{30}$-aryloxy, $C_1$-$C_{20}$-alkylthio, $C_6$-$C_{30}$-arylthio, $SiR^{81}R^{82}R^{83}$, $OR^{81}$, halogen radicals, halogenated $C_1$-$C_{20}$-alkyl radicals, carbonyl (—CO($R^{81}$)), carbonylthio (—C=O($SR^{81}$)), carbonyloxy (—C=O($OR^{81}$)), oxycarbonyl (—OC=O($R^{81}$)), thiocarbonyl (—SC=O($R^{81}$)), amino (—$NR^{81}R^{82}$), pseudohalogen radicals, amido (—C=O($NR^{81}$)), —$NR^{81}$C=O($R^{83}$), phosphonate (—P(O)($OR^{81}$)$_2$, phosphate (—OP(O)($OR^{81}$)$_2$), phosphine (—$PR^{81}R^{82}$), phosphine oxide (—P(O)$R^{81}_2$), sulphate (—OS(O)$_2OR^{81}$), sulphoxide (—S(O)$R^{81}$), sulphonate (—S(O)$_2OR^{81}$), sulphonyl (—S(O)$_2R^{81}$), sulphone amide (—S(O)$_2NR^{81}R^{82}$), $NO_2$, boronic acid esters (—OB($OR^{81}$)$_2$), imino (—C=$NR^{81}R^{82}$)) borane radicals, stannane radicals, hydrazine radicals, hydrazone radicals, oxime radicals, nitroso radicals, diazo radicals, vinyl radicals, sulphoximines, alanes, germanes, boroximes and borazines.

The radicals $R^{81}$, $R^{82}$ and $R^{83}$ in the radicals with donor action or acceptor action have independently of each other the following meanings:

Substituted or unsubstituted $C_1$-$C_{20}$-alkyl or substituted or unsubstituted $C_6$-$C_{30}$-aryl, or $OR^{81}$ wherein suitable and preferred alkyl radicals and aryl radicals are mentioned before. Particularly preferred radicals $R^{81}$, $R^{82}$ and $R^{83}$ are $C_1$-$C_6$-alkyl, e.g. methyl, ethyl or i-propyl or phenyl. In a preferred embodiment—in the case of $SiR^{81}R^{82}R^{83}$—$R^{81}$, $R^{82}$ and $R^{83}$ are preferably independently of each other substituted or unsubstituted $C_1$-$C_{20}$-alkyl or substituted or unsubstituted aryl, preferably phenyl.

Preferred radicals with donor action or acceptor action are selected from the group consisting of:

$C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{81}R^{82}R^{83}$, wherein $R^{81}$, $R^{82}$ and $R^{83}$ are preferably independently of each other substituted or unsubstituted alkyl or substituted oder unsubstituted aryl, preferably phenyl; more preferably at least one of the radicals $R^{81}$, $R^{82}$ or $R^{83}$ is substituted or unsubstituted phenyl, wherein suitable substituents are mentioned before; halogen radicals, preferably F, Cl, more preferably F, halogenated $C_1$-$C_{20}$-alkyl radicals, preferably halogenated $C_1$-$C_6$-alkyl radicals, more preferably fluorinated $C_1$-$C_6$-alkyl radicals, e.g. $CF_3$, $CH_2F$, $CHF_2$ or $C_2F_5$; amino, preferably dimethylamino, diethylamino or diarylamino, more preferably diarylamino; pseudohalogen radicals, preferably CN, —C(O)O$C_1$-$C_4$-alkyl, preferably —C(O)OMe, P(O)$R_2$, more preferably P(O)Ph$_2$.

Particularly preferred radicals with donor action or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{81}R^{82}R^{83}$, wherein suitable radicals $R^{81}$, $R^{82}$ and $R^{83}$ have been already mentioned before, diarylamino ($NR^{84}R^{85}$, wherein $R^{84}$, $R^{85}$ each are $C_6$-$C_{30}$-aryl), —C(O)O$C_1$-$C_4$-alkyl, preferably —C(O)OMe, P(O)Ph$_2$.

A halogen radical is understood to mean preferably F, Cl and Br, more preferably F and Cl, even more preferably F.

A pseudohalogen radical is understood to mean preferably CN, SCN and OCN, more preferably CN.

The radicals with donor action and acceptor action mentioned before do not exclude that further radicals, groups or units mentioned in the present application but not mentioned in the list of radicals with donor action or acceptor action mentioned before may also comprise a donor action or acceptor action.

The heterocycloalkyl radicals, units or groups, alkenyl radicals, units or groups, alkinyl radicals, units or groups, and the groups with donor and/or acceptor action may be substituted or unsubstituted as mentioned before.

An unsubstituted radical, unit or group is understood to mean a radical, unit or group, wherein the substitutable atoms of said radical, unit or group comprise hydrogen atoms. A substituted radical, unit or group is understood to mean a radical, unit or group wherein one or more substitutable atom(s) comprise at least one position a substituent instead of a hydrogen atom. Suitable substituents are the same substituents as mentioned before concerning the aryl radicals, units or groups.

In the case that radicals having an identical numbering are mentioned more than once in the compounds of the present invention, said radicals may have independently of each other the meaning mentioned in the definition of the radical.

The radical X in the compounds of formula (V) is understood to mean NR, S, O or PR, preferably NR, S or O, more preferably O or S, even more preferably O.

The radical R is understood to mean aryl, heteroaryl, alkyl, cycloalkyl or heterocycloalkyl, preferably aryl, heteroaryl or alkyl, more preferably aryl, wherein the residues mentioned before may be substituted or unsubstituted. Suitable substituents are mentioned before. Particularly preferably the radical R is understood to mean phenyl, which may be substituted with one or more of the substituents mentioned before or unsubstituted. Even more particularly preferably the radical R is understood to mean unsubstituted phenyl.

The radical B in the compounds of formula (V) is understood to mean —NR$^{20}$R$^{21}$, P(O)R$^{22}$R$^{23}$, —PR$^{24}$R$^{25}$, —S(O)$_2$R$^{26}$, —S(O)R$^{27}$, —SR$^{26}$ or —OR$^{29}$; preferably NR$^{2}$OR$^{21}$, —P(O)R$^{22}$R$^{23}$ or —OR$^{29}$, more preferably —NR$^{20}$R$^{21}$.

The radicals R$^{20}$ tos R$^{29}$ and R$^{74}$ to R$^{76}$ have the following meanings:

R$^{20}$, R$^{21}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;

R$^{22}$, R$^{23}$, R$^{24}$, R$^{25}$, R$^{26}$, R$^{27}$, R$^{28}$, R$^{29}$, R$^{74}$, R$^{75}$, R$^{76}$
are each independently aryl, heteroaryl, alkyl, cycloalkyl or heterocycloalkyl, preferably aryl or heteroaryl, wherein the radicals are unsubstituted or substituted with one or more radicals selected from alkyl, cycloalkyl, heterocycloalkyl, aryl, heteroaryl and a group with donor action or acceptor action, more preferably unsubstituted or substituted phenyl, wherein suitable substituents are mentioned before, e.g. tolyl or a group of the formula

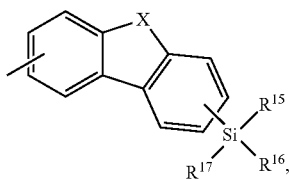

in which the group X and the radicals R$^{15}$, R$^{16}$ and R$^{17}$ independently of each other have the meanings mentioned concering the compounds of formula (II) or (II*).

Particularly preferably R$^{22}$, R$^{23}$, R$^{24}$, R$^{25}$, R$^{26}$, R$^{27}$, R$^{28}$ and R$^{29}$ are understood to mean independently of each other phenyl, tolyl or a group of the formula

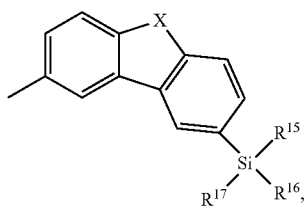

in which X is NPh, S or O.

Examples of preferred groups —NR$^{20}$R$^{21}$ are selected from the group consisting of pyrrolyl, 2,5-dihydro-1-pyrrolyl, pyrrolidinyl, indolyl, indolinyl, isoindolinyl, carbazolyl, azacarbazolyl, diazacarbazolyl, imidazolyl, imidazolinyl, benzimidazolyl, pyrazolyl, indazolyl, 1,2,3-triazolyl, benzotriazolyl, 1,2,4-triazolyl, tetrazolyl, 1,3-oxazolyl, 1,3-thiazolyl, piperidyl, morpholinyl, 9,10-dihydroacridinyl and 1,4-oxazinyl, wherein the groups mentioned before may be unsubstituted or substituted with one or more substituents selected from alkyl, cycloalkyl, heterocycloalkyl, aryl, heteroaryl and a group with donor action or acceptor action, preferably, the group —NR$^{6}$R$^{7}$ is selected from carbazolyl, pyrrolyl, indolyl, imidazolyl, benzimidazolyl, azacarbazolyl and diazacarbazolyl, wherein the groups mentioned before may be unsubstituted or substituted with one or more substituents selected from alkyl, cycloalkyl, heterocycloalkyl, aryl, heteroaryl and a group with donor action or acceptor action, more preferably, the group —NR$^{20}$R$^{21}$ is understood to mean carbazolyl, which may be may be unsubstituted or substituted with one or more substituents selected from alkyl, cycloalkyl, heterocycloalkyl, aryl, heteroaryl and a group with donor action or acceptor action.

Particularly preferred groups —NR$^{20}$R$^{21}$ are:

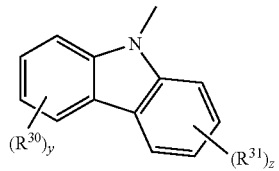

in which

R$^{30}$, R$^{31}$ are independently of each other alkyl, cycloalkyl, heterocycloalkyl, aryl or heteroaryl; preferably methyl, carbazolyl, dibenzofuryl or dibenzothienyl;

y, z are independently of each other 0, 1, 2, 3 or 4, preferably 0 or 1;

for example:

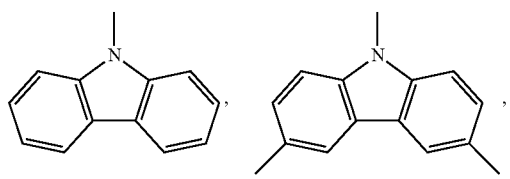

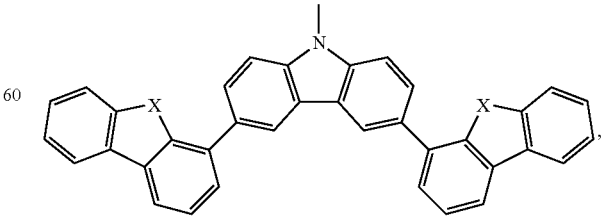

wherein X is NPh, S oder O;

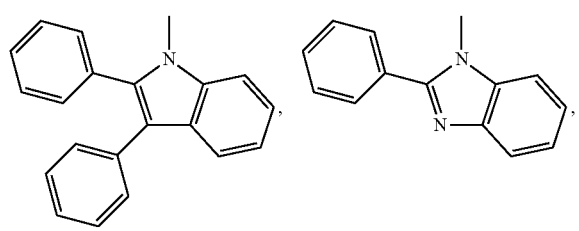
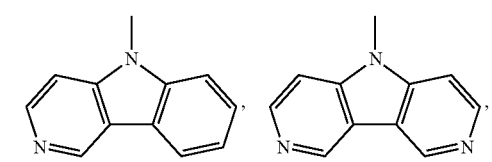
wherein X is NPh, S or O,
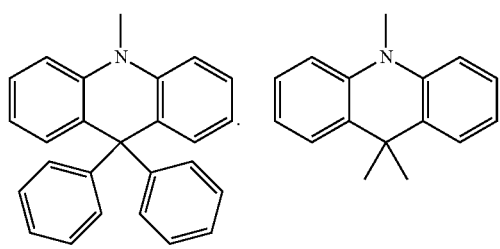
Particularly preferred groups —P(O)R$^{22}$R$^{23}$ are:
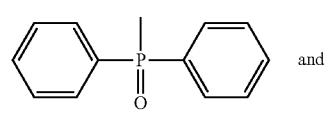
and
An even more particularly preferred group —PR$^{24}$R$^{25}$ is:
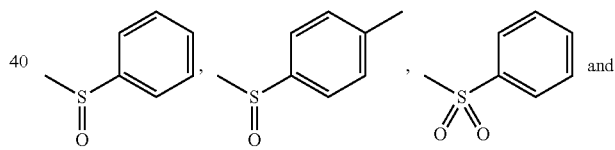
Particularly preferred groups —S(O)$_2$R$^{26}$ and —S(O)R$^{27}$ are:
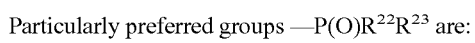
and
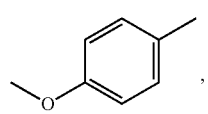
Particularly preferred groups —SR$^{28}$ and —OR$^{29}$ are:

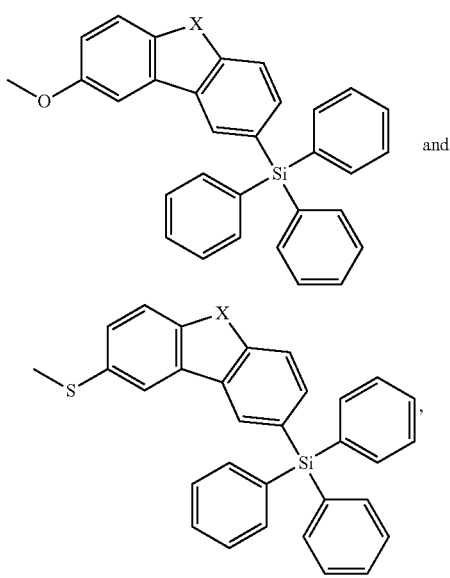

wherein X is in each case NPh, S or O.

$R^{18}$, $R^{19}$ in the compounds of formula (V) are understood to mean independently of each other alkyl, cycloalkyl, heterocycloalkyl, aryl, heteroaryl, a further group B or a group with donor action or acceptor action; preferably, independently of each other alkyl, aryl, heteroaryl or a group with donor action or acceptor action. $R^{18}$ or $R^{19}$ are for example understood to mean independently of each other:

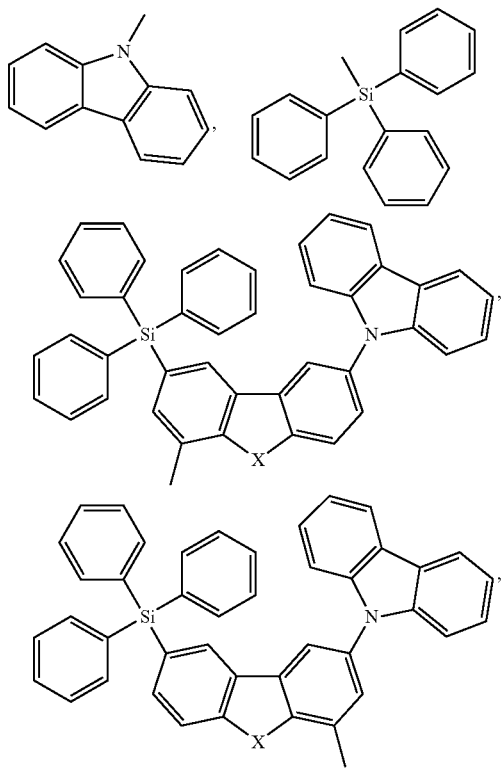

wherein X is NPh, S or O.

In the compounds of formula (V) there may be o groups $R^{18}$ and/or p groups $R^{19}$, wherein
o is 0, 1, 2, 3 or 4; preferably 0, 1 or 2;
p is 0, 1, 2, or 3; preferably 0, 1 or 2.
Particularly preferably at least o or p is 0, even more particularly preferably o and p are 0 or o is 1 and p is 0.

$R^{73}$ is understood to mean in the compounds of the general formula (II) in general independently of each other $SiR^{74}R^{75}R^{76}$, aryl, heteroaryl, alkyl, cycloalkyl or heterocycloalkyl, optionally substituted with a group $OR^{77}$.

$R^{77}$ is understood to mean in the compounds of the general formula (II) in general independently of each other aryl, heteroaryl, alkyl, cycloalkyl or heterocycloalkyl.

In a further embodiment two units oft the general formula (II) and/or (II*) are linked via a linear or branched, saturated or unsaturated bridge, which is optionally interrupted by at least one hetero atom, via a bond or via O, wherein said bridge is linked to the Si atoms instead of $R^{16}$ in the general formulae (II) and/or (II*).

Preferably, said bridge is selected from the group consisting of —$CH_2$—, —$C_2H_4$—, —$C_3H_6$—, —$C_4H_8$—, —$C_6H_{12}$—, —$C_8H_{16}$—, —$C_9H_{18}$—, —$CH(C_8H_{17})CH_2$—, —$C_2H_4(CF_2)_8C_2H_4$—, —C≡C—, -1,4-$(CH_2)_2$-Phenyl-$(CH_2)_2$—, 1,3-$(CH_2)_2$-Phenyl-$(CH_2)_2$—, -1,4-Phenyl-, -1,3-Phenyl-, —O—, —O—$Si(CH_3)_2$—O—, —O—$Si(CH_3)_2$—O—$Si(CH_3)_2$—O— and —O—

In a preferred embodiment of the present invention the compounds of the general formula (V) have the general formula (IIa), (IIb), (IIc), (IId) or (IIe), i.e. the following compounds are preferred embodiments of the compounds of the general formulae (II) or (II*):

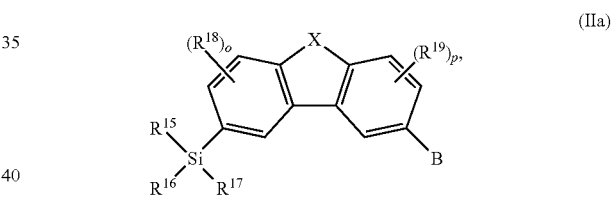

(IIa)

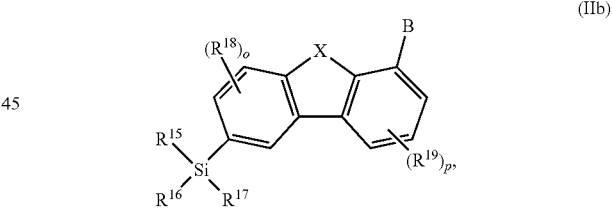

(IIb)

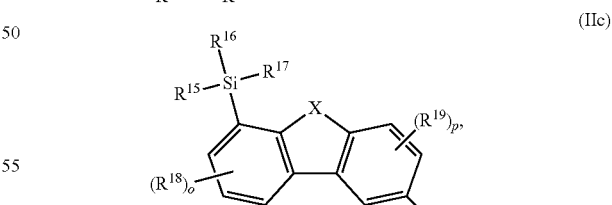

(IIc)

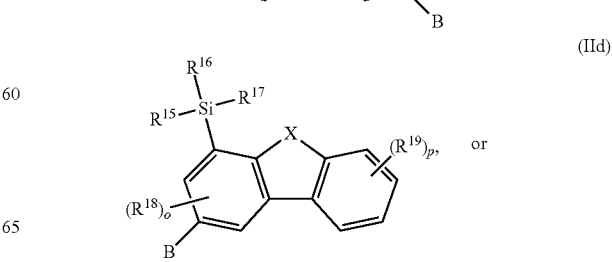

(IId)

or

-continued

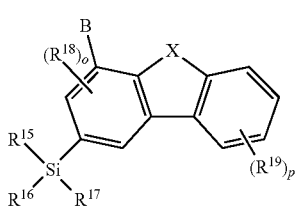
(IIe)

wherein the radicals and groups B, X, $R^{15}$, $R^{16}$, $R^{17}$, $R^{18}$, $R^{19}$ as well as o and p having the meanings mentioned before.

In a further preferred embodiment the radicals $R^{15}$, $R^{16}$ or $R^{17}$ in the compounds of the general formulae (II) or (II*) are understood to mean aromatic units of the general formulae (IIi) and/or (IIi*)

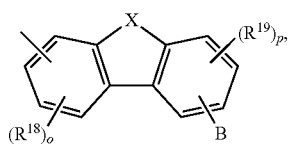
(IIi)

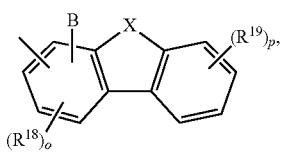
(IIi*)

wherein $R^{18}$, $R^{19}$, B, X, o and p have the meanings as mentioned above.

Therefore, in one embodiment the present invention concerns an OLED of the present invention, wherein in the compounds of the general formulae (II) or (II*) the radicals $R^{15}$, $R^{16}$ or $R^{17}$ are aromatic units of the general formulae (IIi) and/or (IIi*)

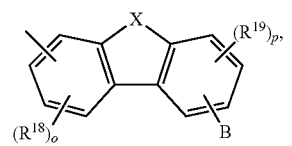
(IIi)

(IIi*)

wherein $R^{18}$, $R^{19}$, B, X, o and p have the meanings as mentioned above.

Advantageous OLEDs comprise a compound of the general formula (II) or (II*) selected from the following group:

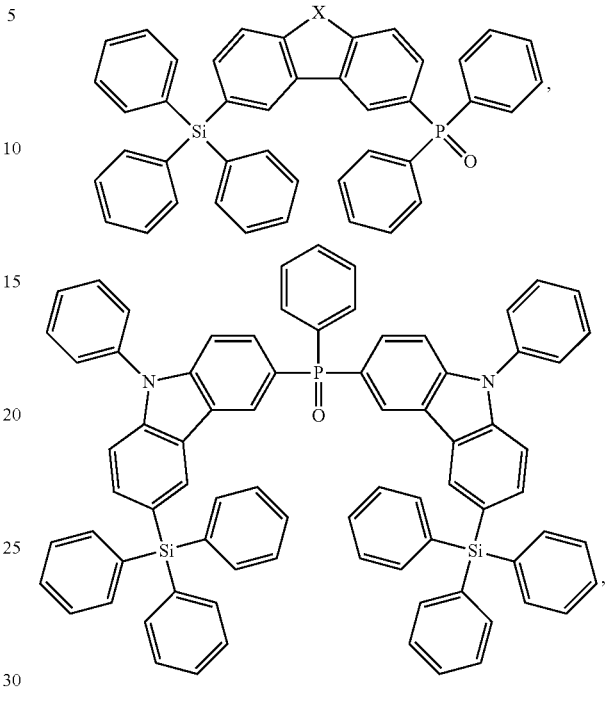

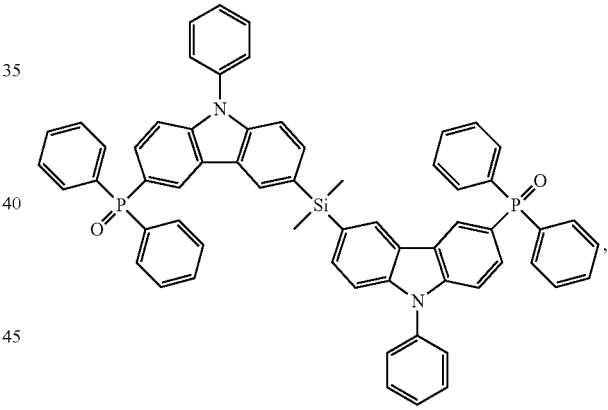

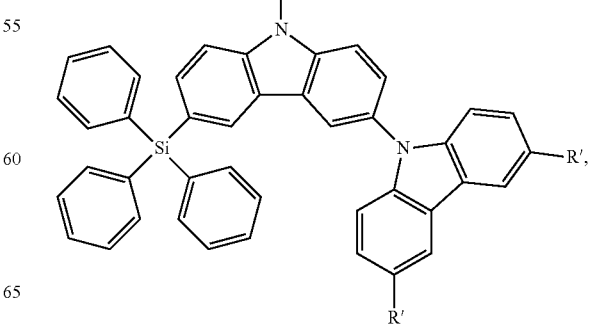

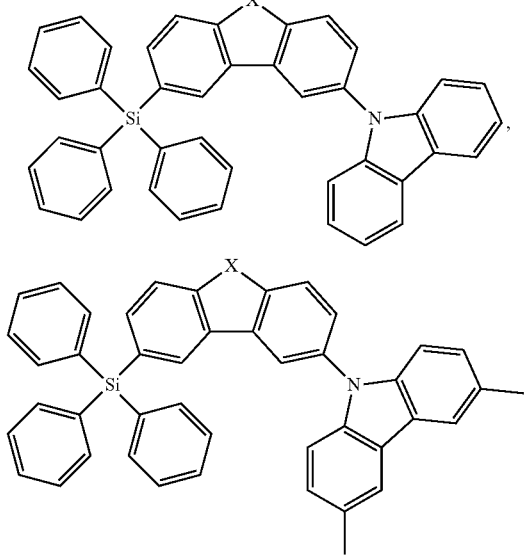
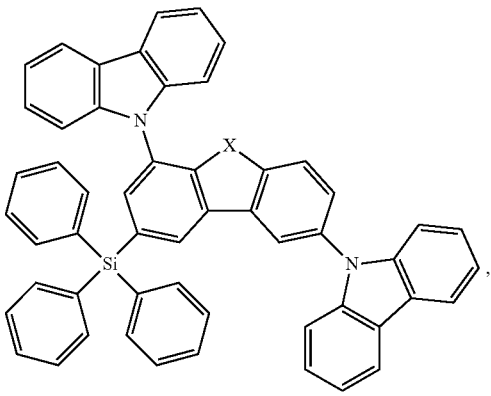
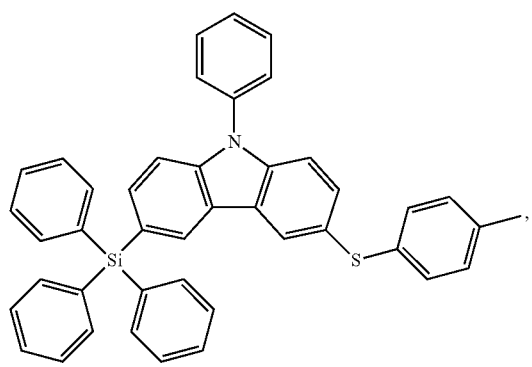
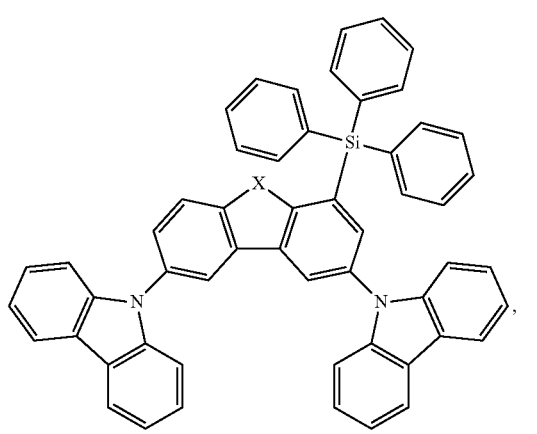
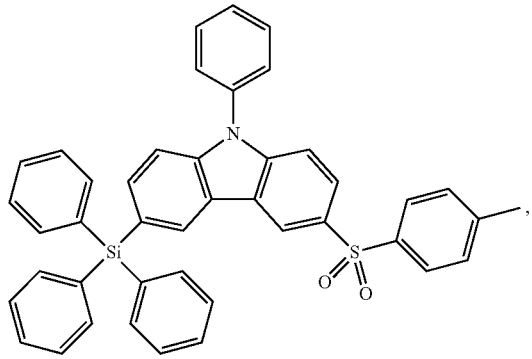
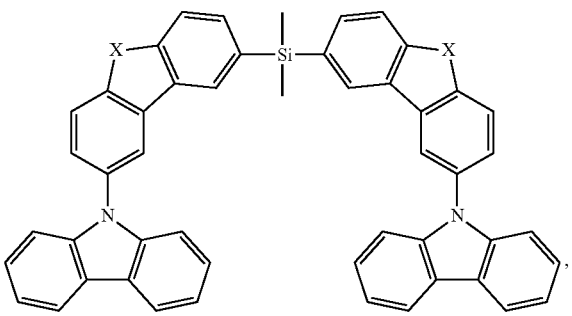
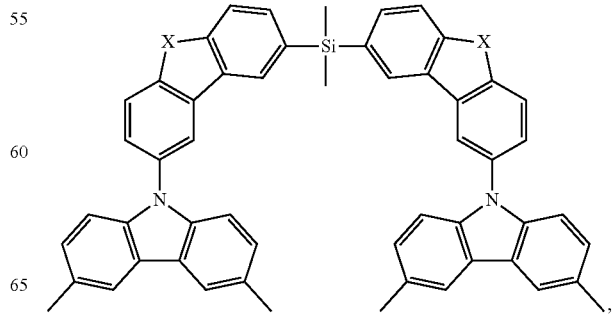

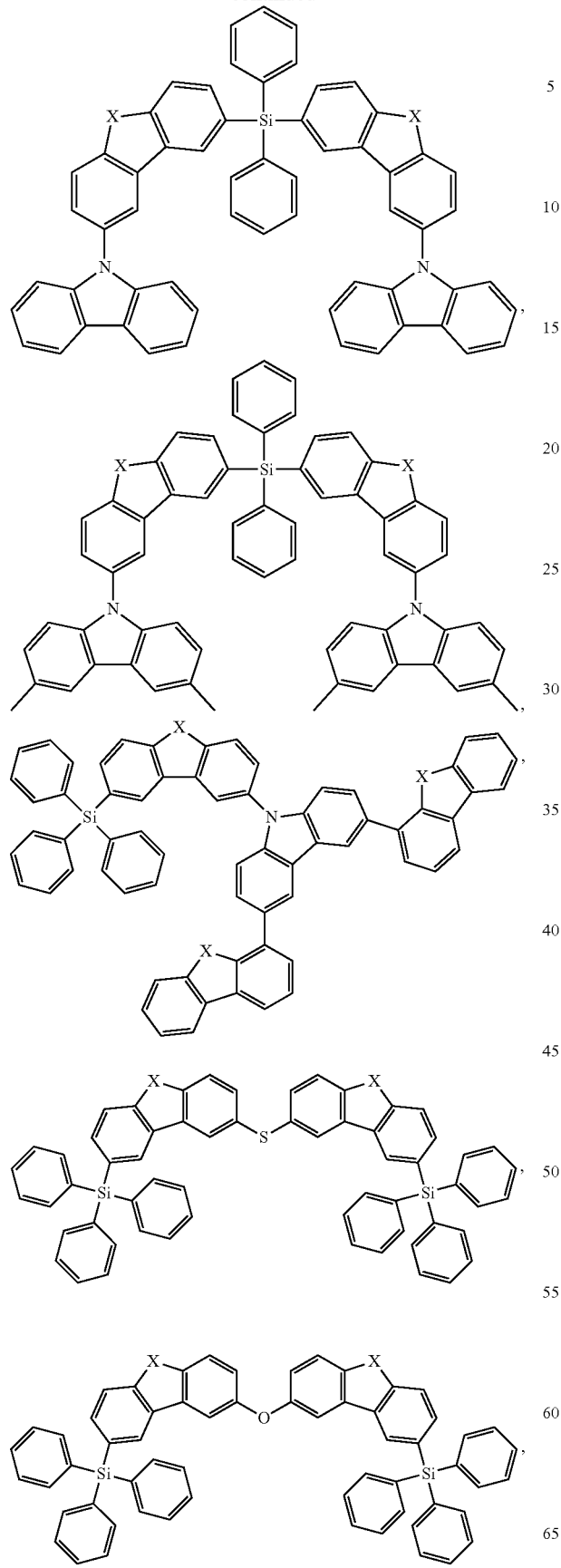
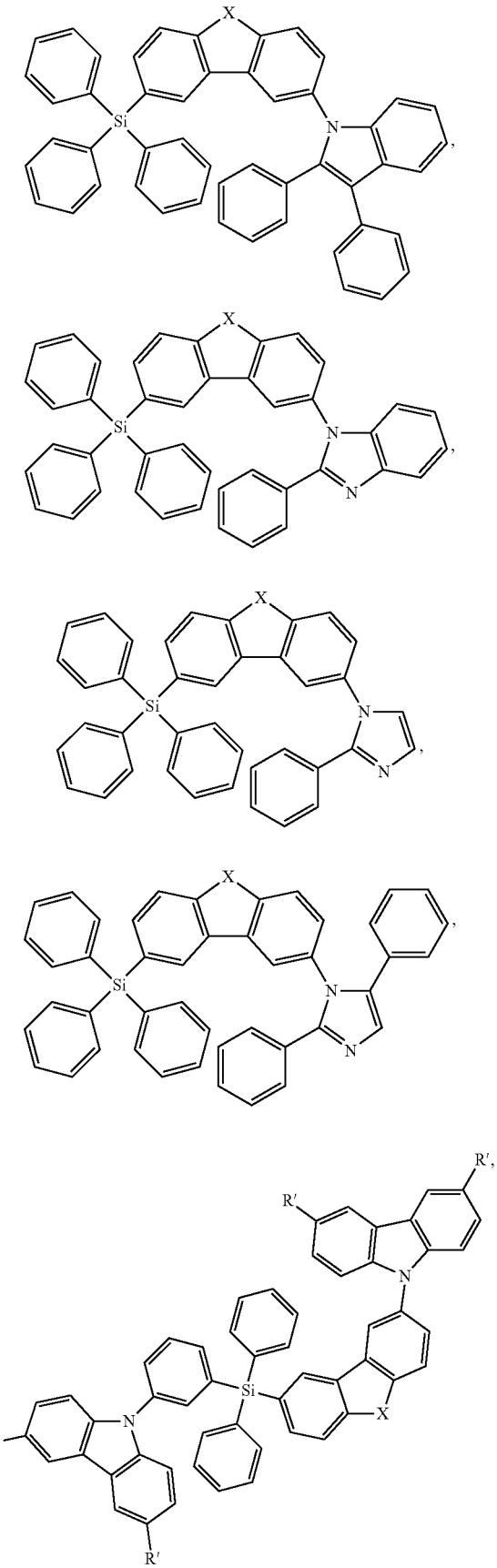

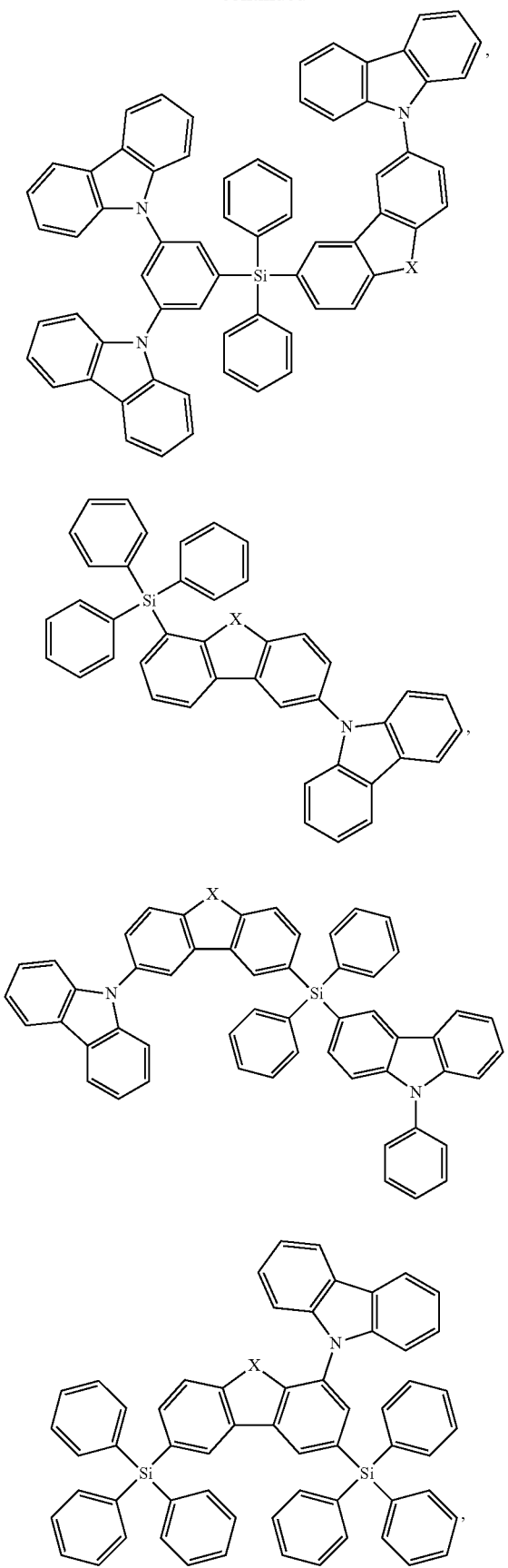
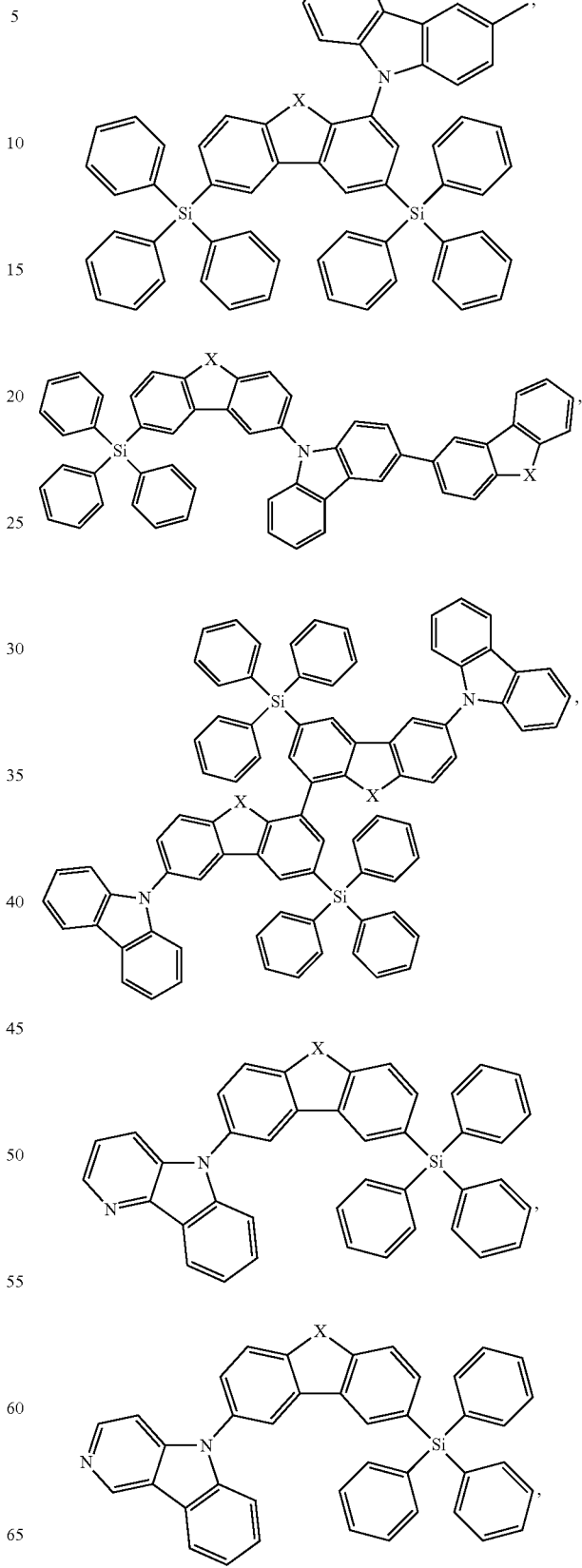

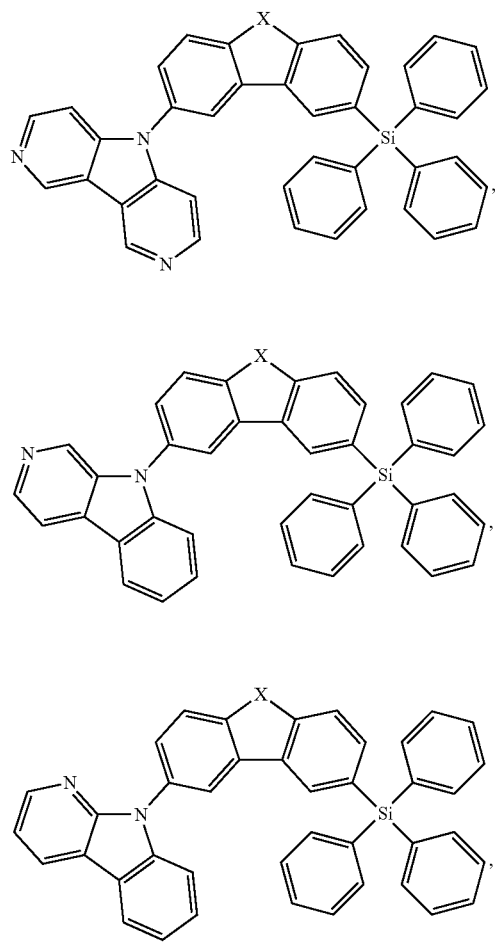
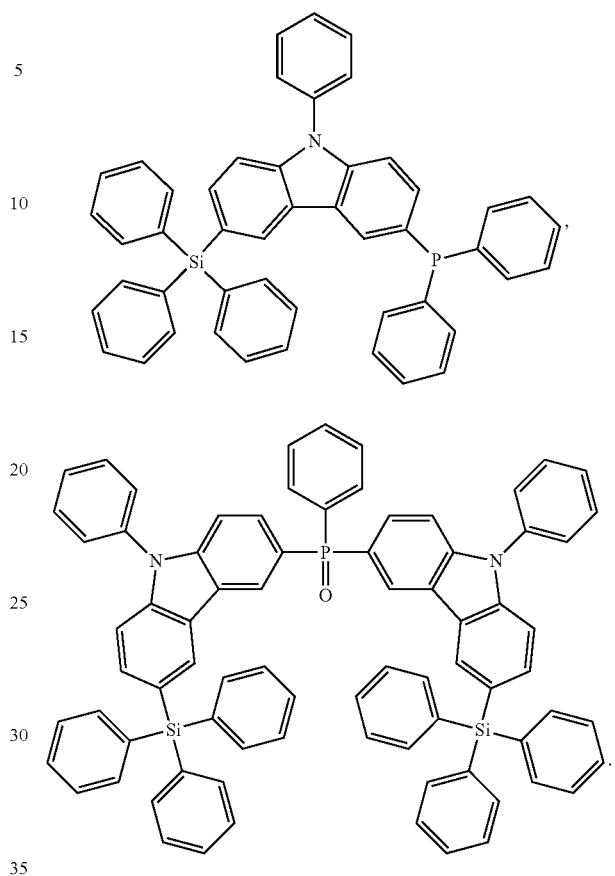
in which X is S or O and R' is hydrogen or methyl, and mixtures thereof.
Further particularly preferred compounds of the general formulae (II) or (II*) are:
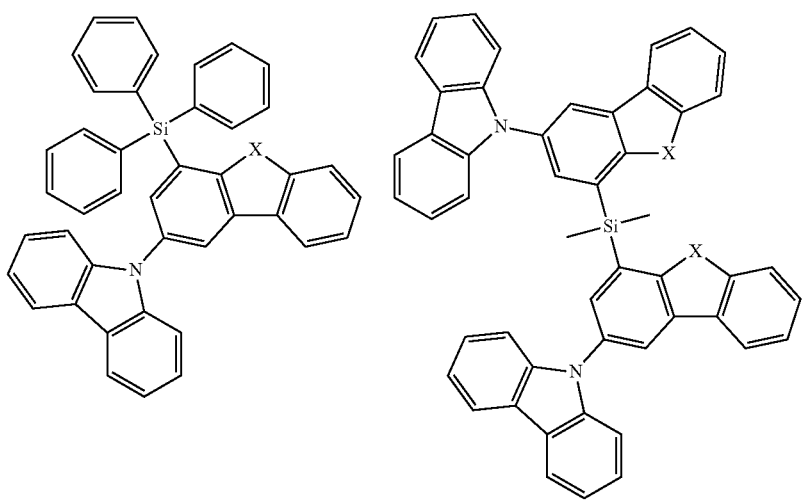

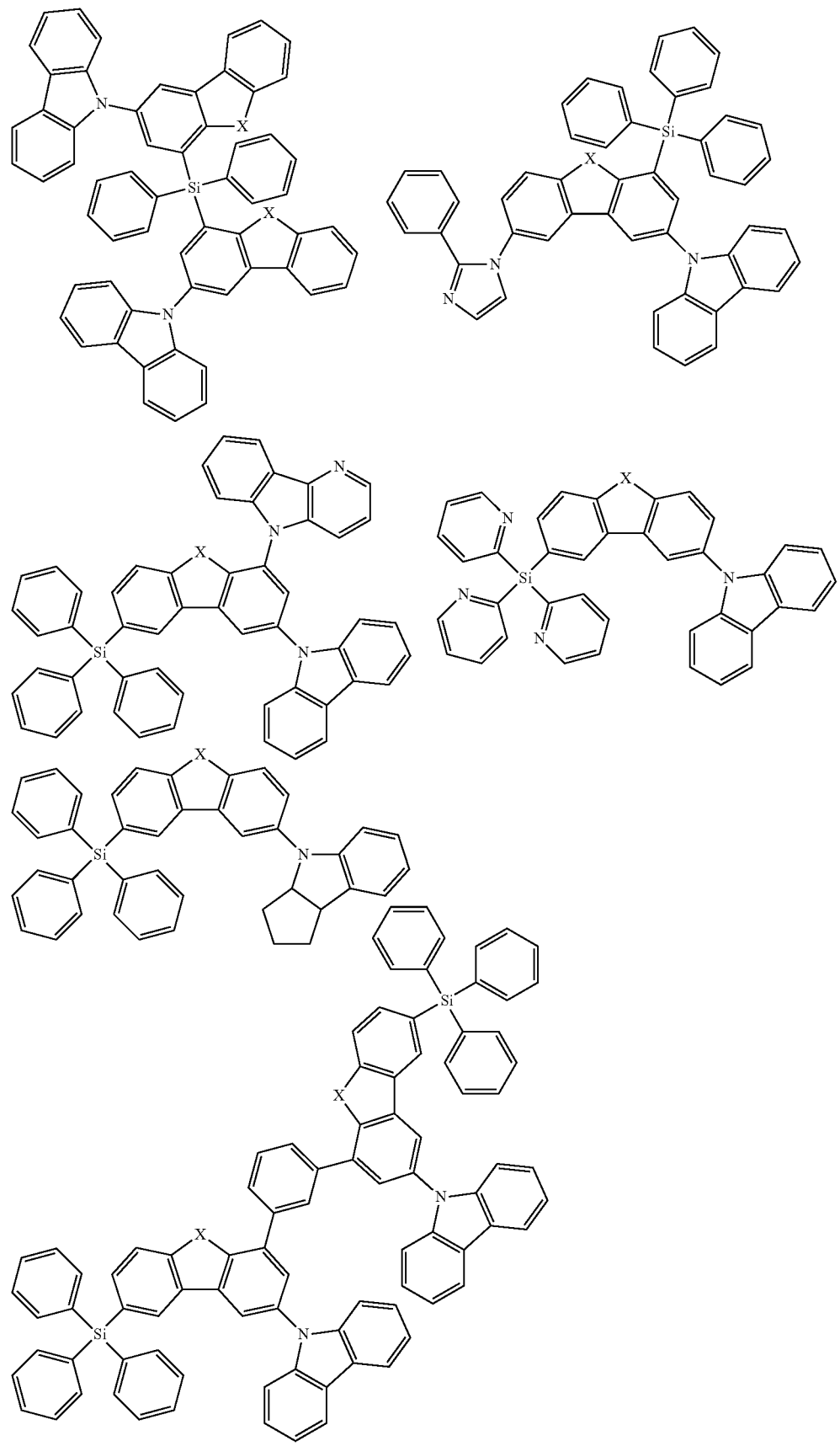

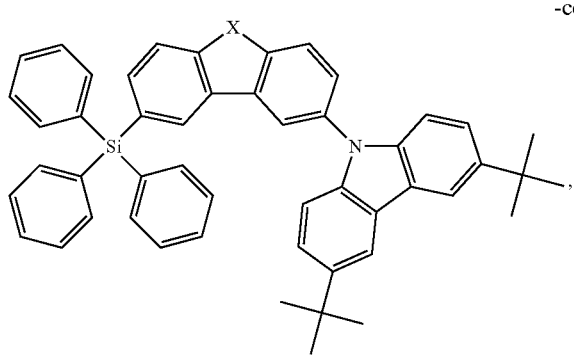
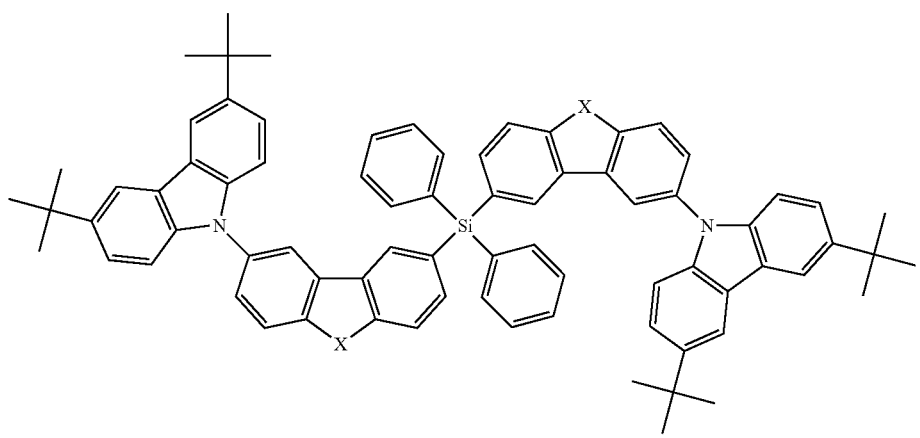
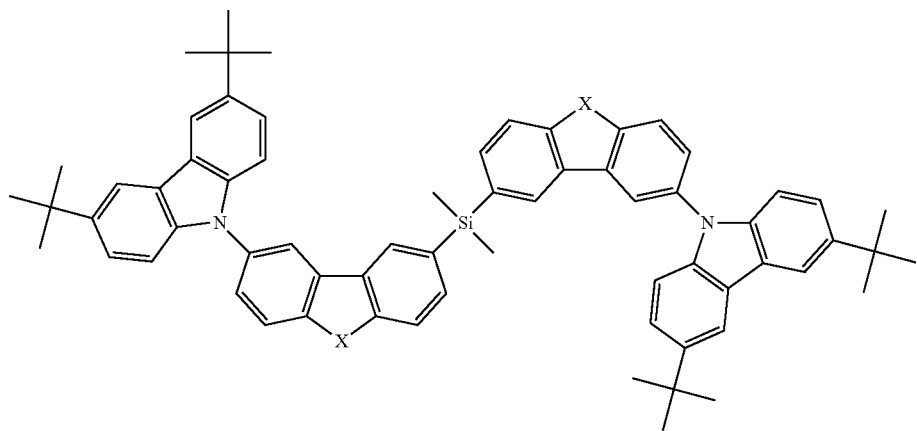
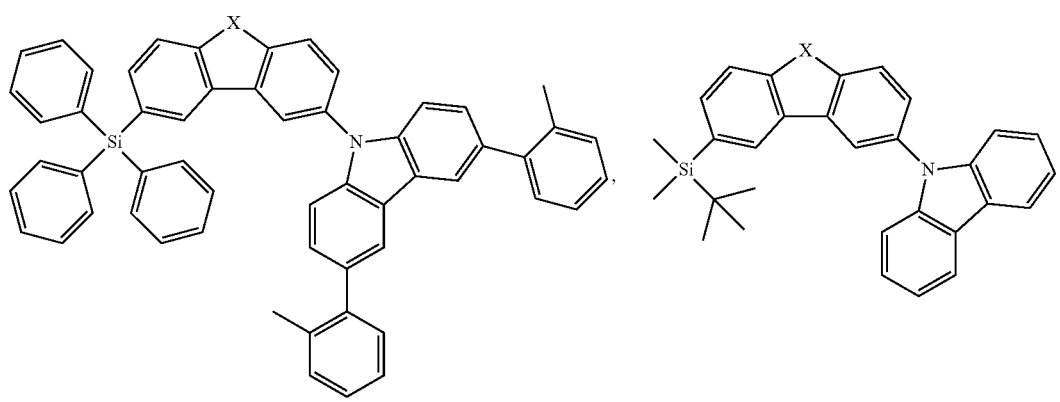

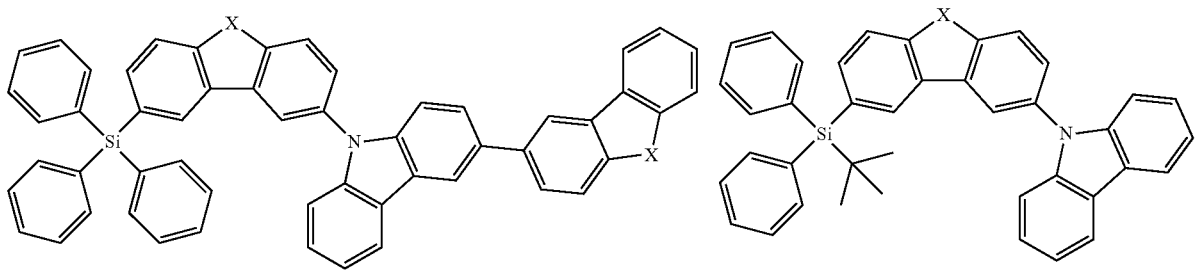
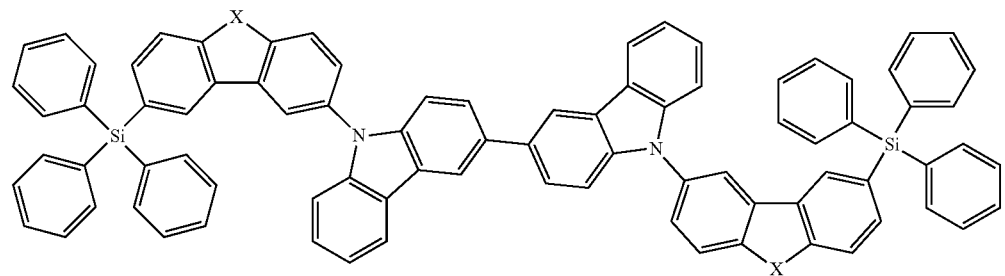
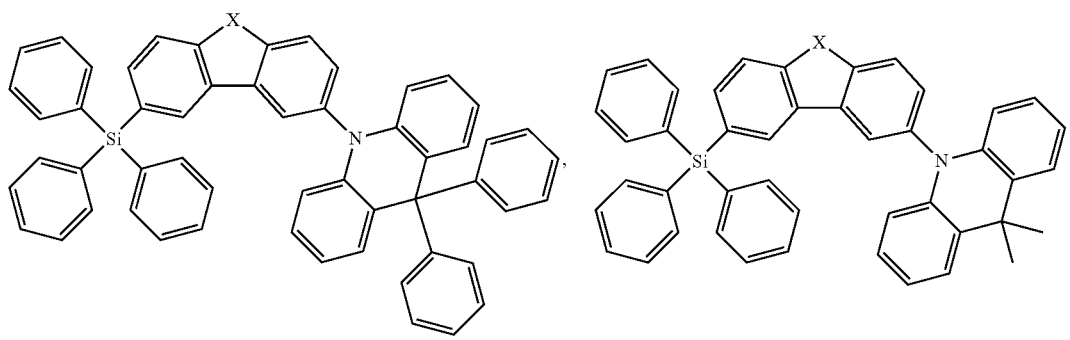
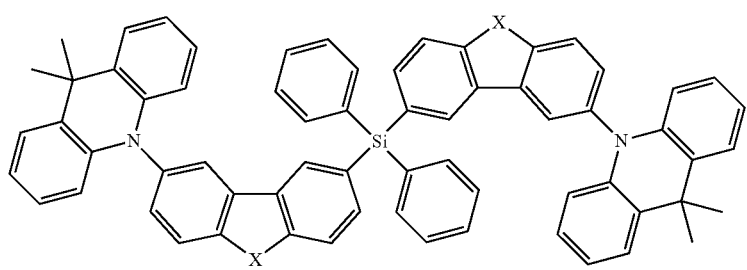
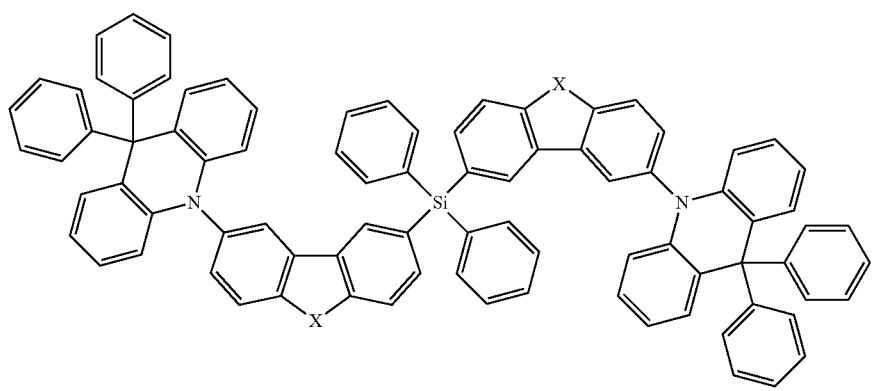

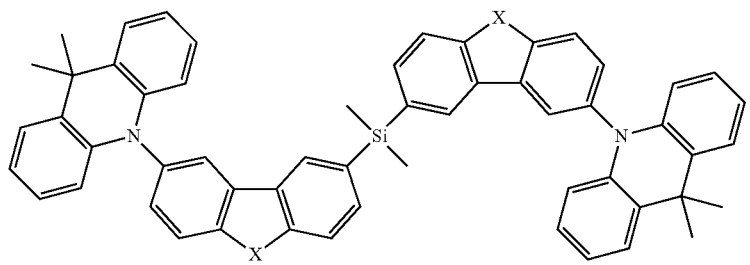

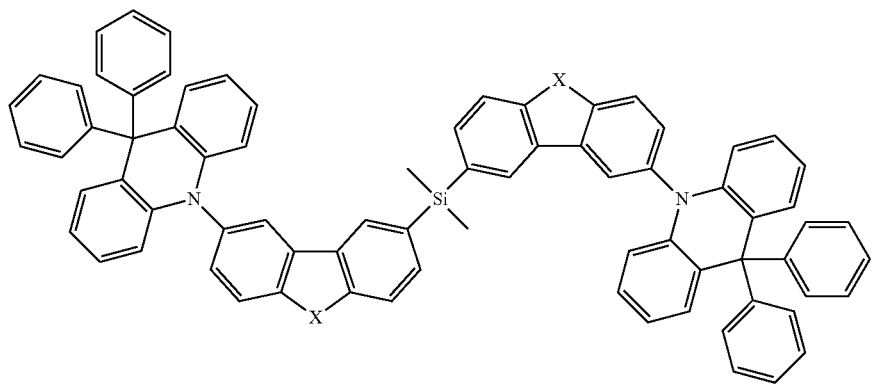

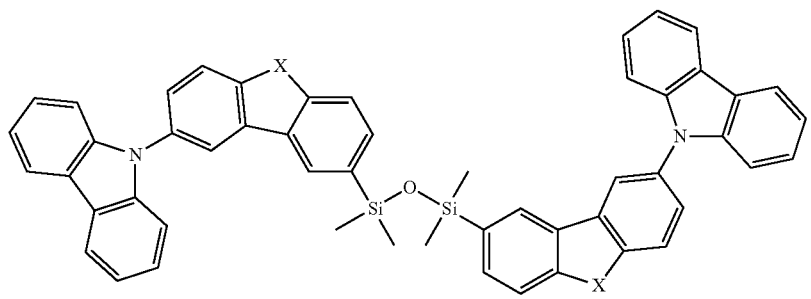

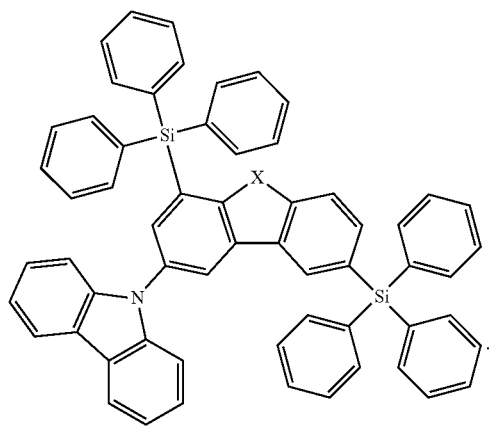

Also, in said particularly preferred compounds of the general formulae (II) or (II*) X is O or S, preferably O.

In an even more particularly preferred embodiment the present invention concerns an OLED comprising besides at least one metal carbene complex of the general formula (I) at least one compound of the general formula (V), wherein the compound of the general formula (V) is most preferably at least one of the compounds mentioned below.

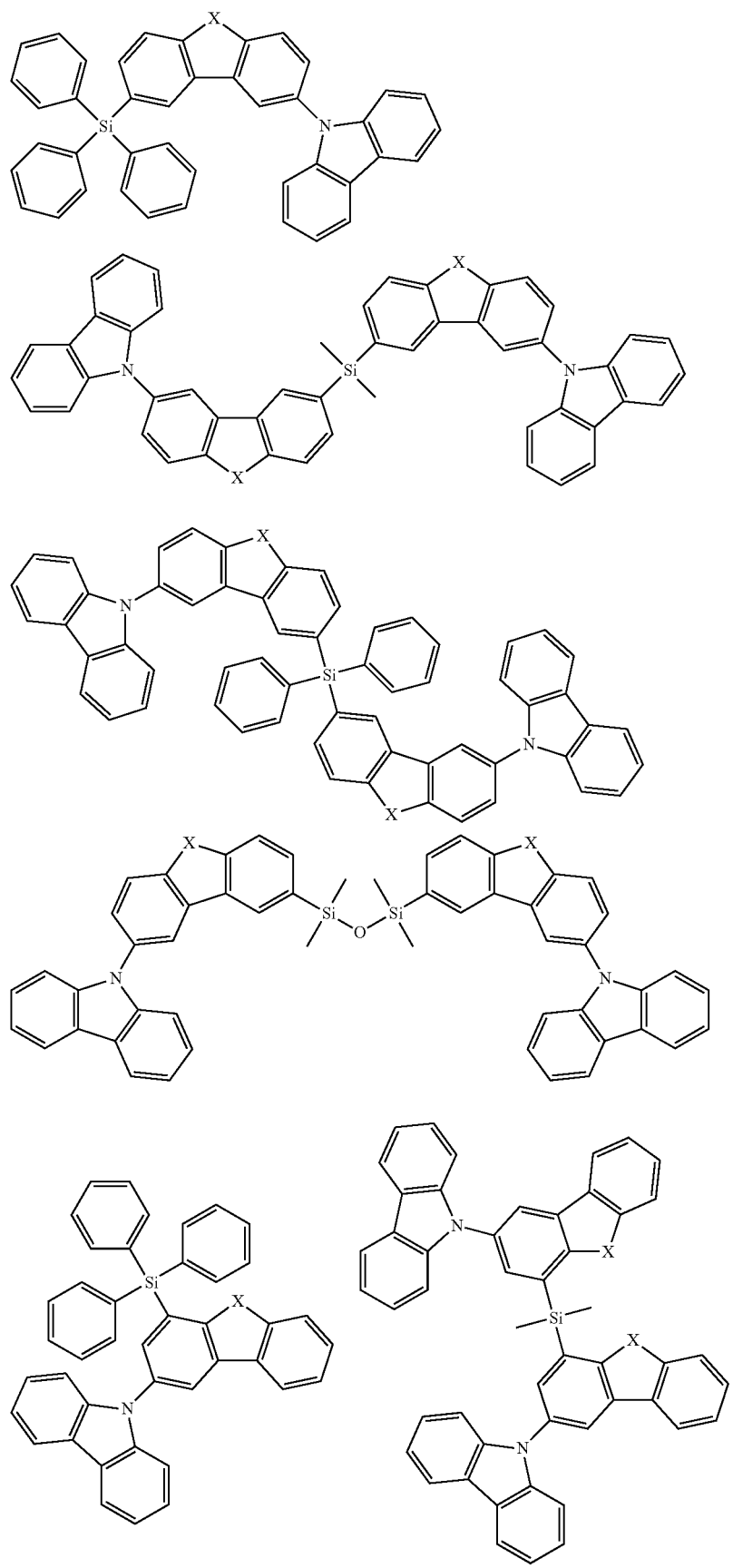

-continued
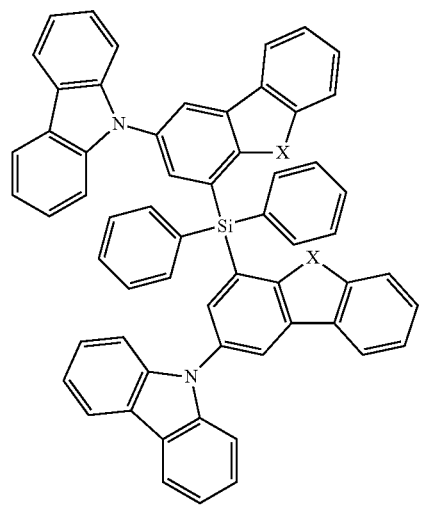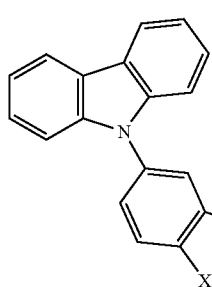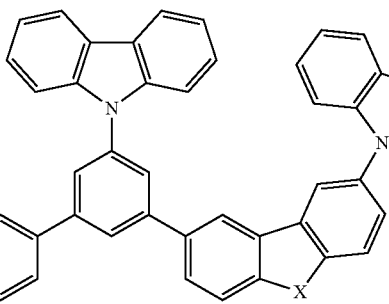
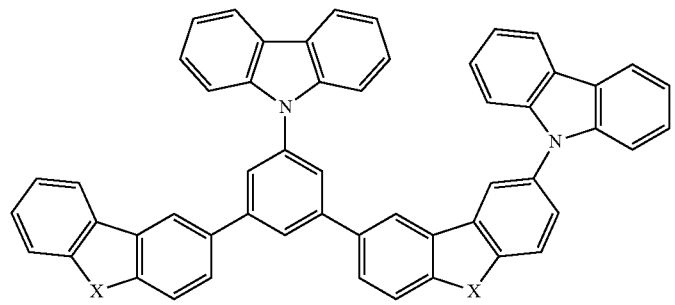
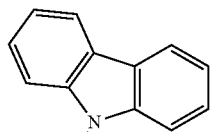
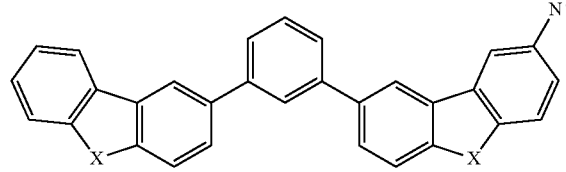
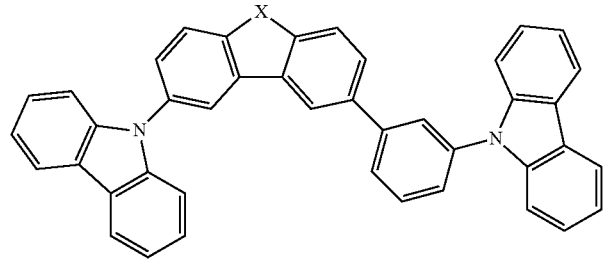
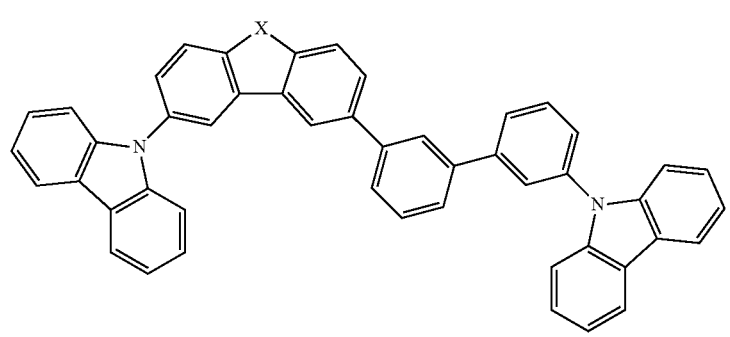

-continued
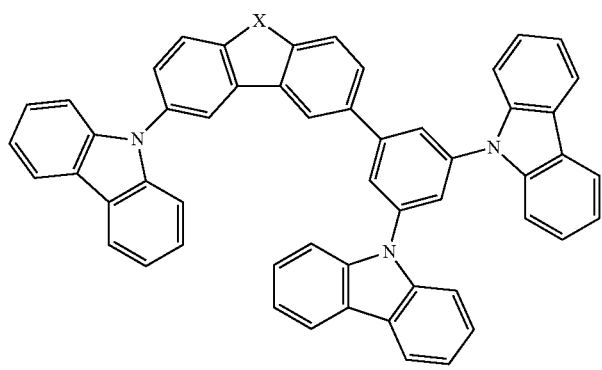
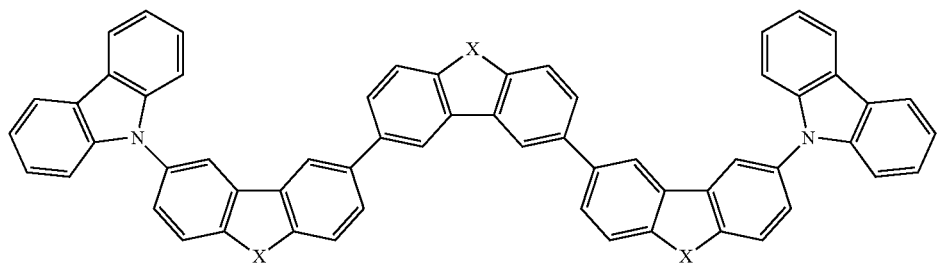
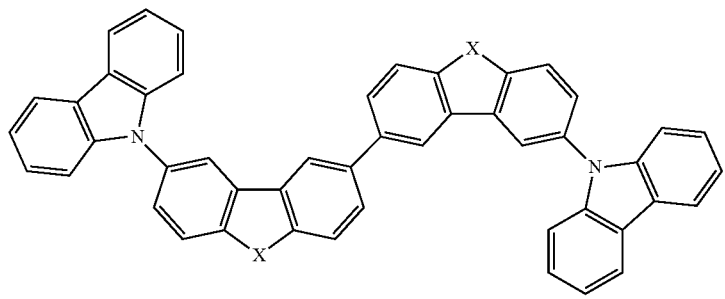
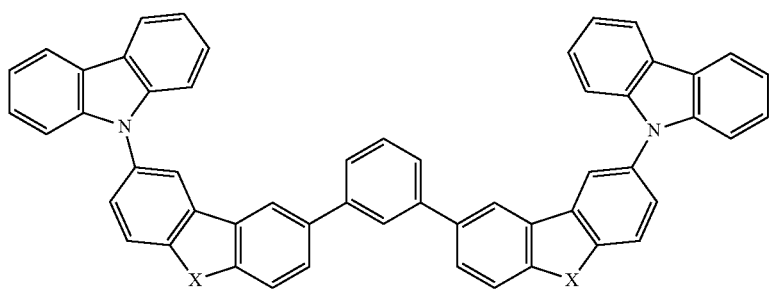
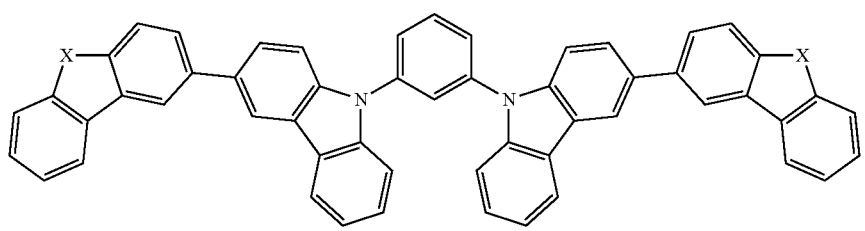

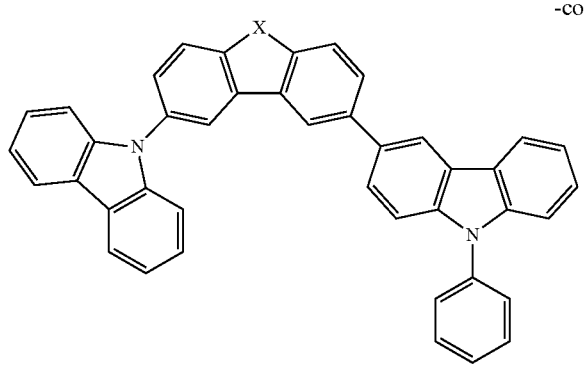
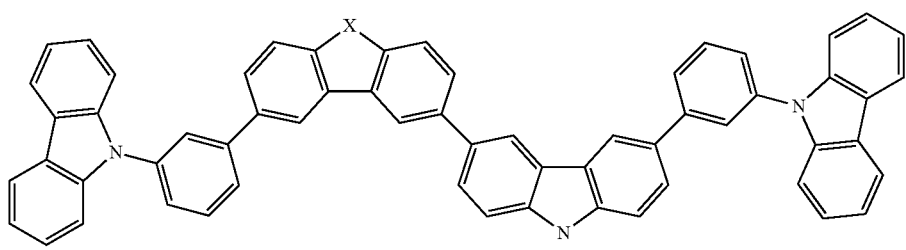
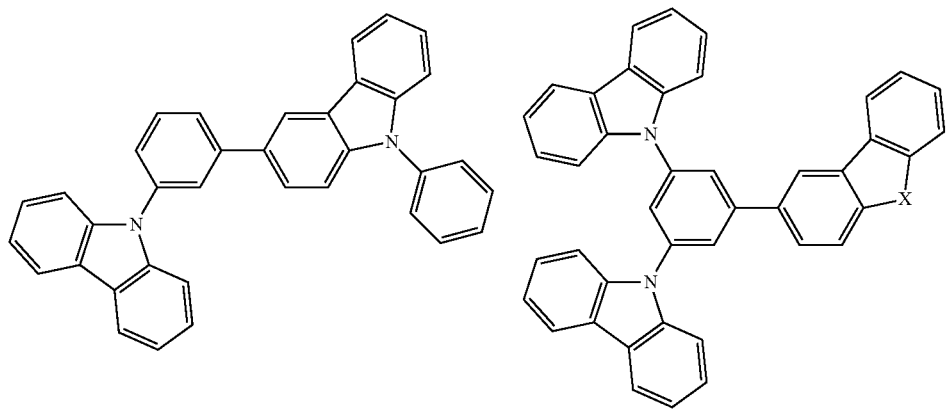
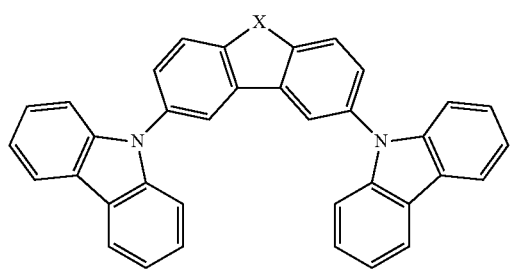
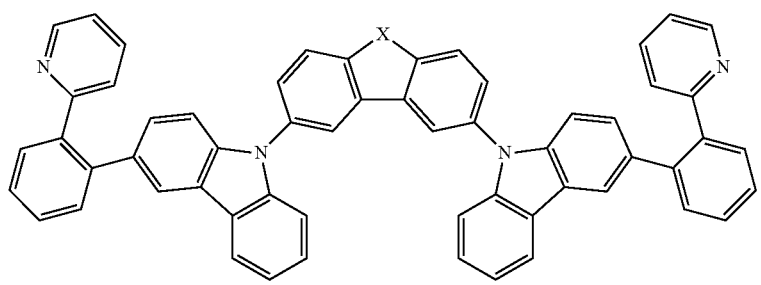

-continued
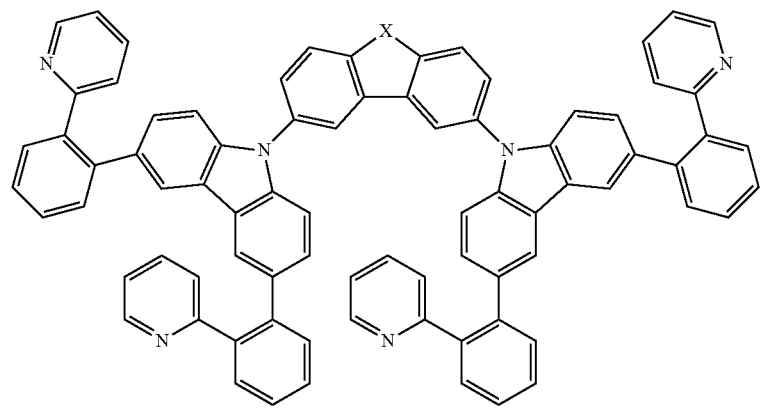
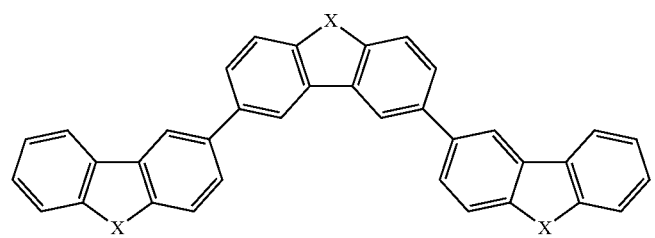
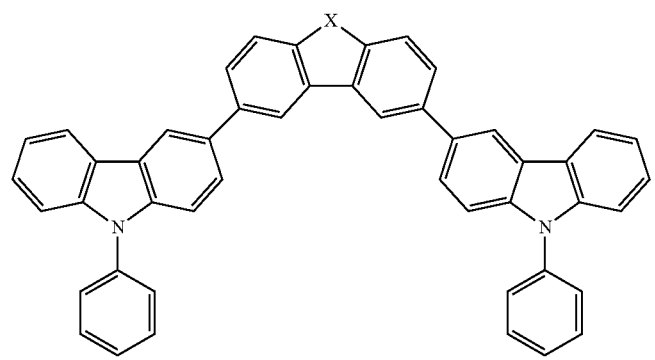
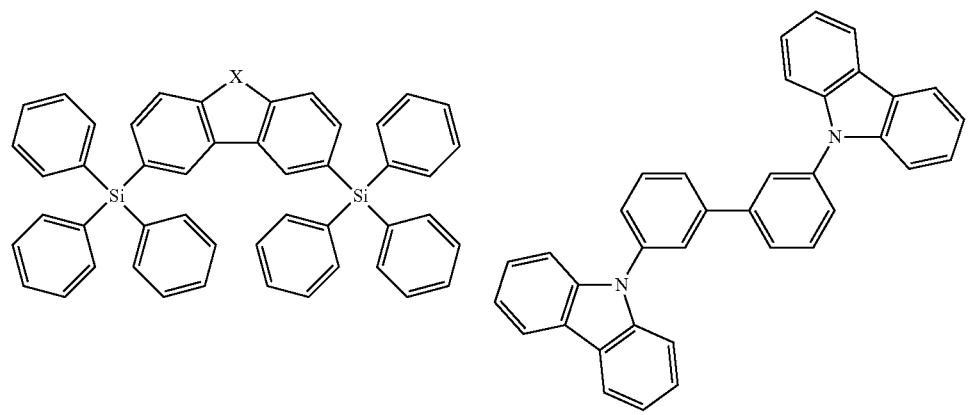
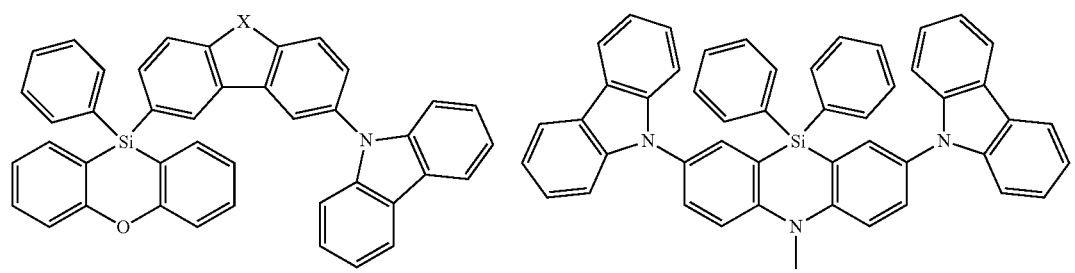

-continued

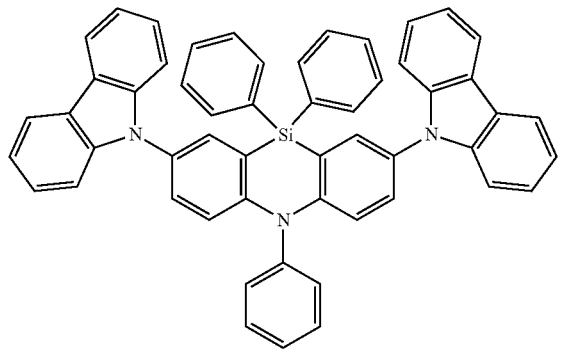
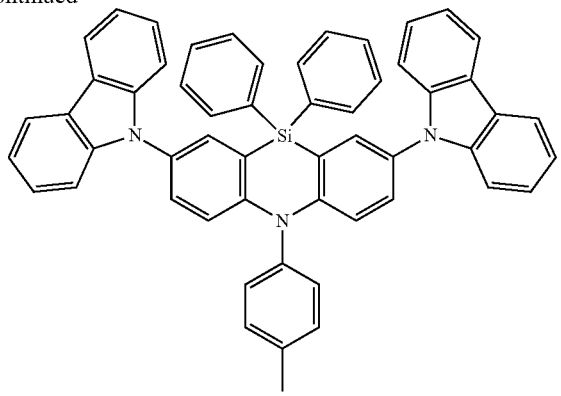

In the compounds mentioned before X is O or S, preferably O. In the case that more than one X is present in the molecule all groups X have the same meaning.

Beside the compounds of formula (V) crosslinked or polymeric materials comprising repeating units of the general formula (V) in cross linked or polymerized form may be used together with at least one metal carbene complex of the general formula (I). Said crosslinked or polymeric materials are preferably used as matrix materials and/or hole/exciton blockers—as the compounds of formula (V).

The crosslinked or polymeric materials show a superior solubility in organic solvents, superior film forming properties and relatively high glass transition temperatures. Additionally, a high mobility of charge carriers, a high stability of color emission and a long operative time of the corresponding devices is observed in the case that crosslinked or polymeric materials according to the present invention are used in organic light emitting diodes (OLEDs).

The crosslinked or polymeric materials are especially useful as coatings or in thin films, because said materials are thermically and mechanically stable and relatively free of defects.

The crosslinked or polymeric materials comprising repeating units of the general formula (V) may be prepared by a process comprising Steps (a) and (b):
(a) Preparation of a crosslinkable or polymerizable compound of the general formula (V), wherein at least one of the o radicals R18 or at least one of the radicals R19 is a crosslinkable or polymerizable group linked by a spacer, and
(b) Crosslinking or polymerization of the compound of the general formula (V) obtained in step (a).

The crosslinked or polymeric materials may be homopolymers, i.e. exclusively units of the general formula (V) are present in crosslinked or polymerized form. The crosslinked or polymeric materials may also be, i.e. beside the units of the general formula (V) further monomers are present in crosslinked or polymerized form, for example monomers having hole transporting and/or electron transporting properties.

The compounds of formula (V) may for example be prepared as described in the processes mentioned in WO2010079051, WO2007/077810, JP2009267255 respectively US20090017331 A1 or in analog processes.

In a further preferred embodiment the OLED of the present invention comprises a light emitting layer comprising at least one inventive metal carbene complex of formula (I), at least one matrix material of formula (V), and optionally at least one further hole transporting matrix material.

In a further preferred embodiment the present invention concerns an OLED comprising at least one inventive heteroleptic metal carbene complex of formula (I) as well as at least one compound of the general formula (VI)

(VI)

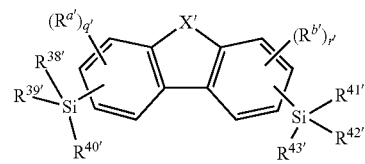

in which:
X' is $NR^{37'}$, S, O, $PR^{37'}$, $SO_2$ or SO;
$R^{37'}$ is substituted or unsubstituted $C_1$-$C_{20}$-alkyl, substituted or unsubstituted $C_6$-$C_{30}$-aryl, or substituted or unsubstituted heteroaryl having from 5 to 30 ring atoms;
$R^{38'}$, $R^{39'}$, $R^{40'}$, $R^{41'}$, $R^{42'}$, $R^{43'}$
are each independently substituted or unsubstituted $C_1$-$C_{20}$-alkyl, or substituted or unsubstituted $C_6$-$C_{30}$-aryl, or a structure of the general formula (c)

(c)

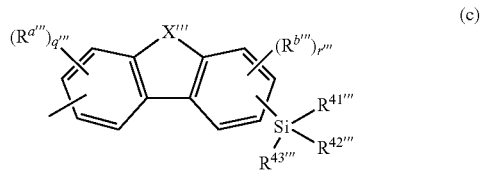

$R^{a'}$, $R^{b'}$
are each independently substituted or unsubstituted $C_1$-$C_{20}$-alkyl, substituted or unsubstituted $C_6$-$C_{30}$-aryl, or substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^{34'}R^{35'}R^{36'}$, halogen radicals, halogenated $C_1$-$C_{20}$-alkyl radicals, carbonyl (—CO($R^{34'}$)), carbonylthio (—C=O($SR^{34'}$)), carbonyloxy (—C=O (OR$^{34'}$)), oxycarbonyl (—OC=O(R$^{34'}$)), thiocarbonyl (—SC=O(R$^{34'}$)), amino (—NR$^{34'}$R$^{35'}$), OH, pseudohalogen radicals, amido (—C=O(NR$^{34'}$)), —NR$^{34'}$C=O(R$^{35'}$), phosphonate (—P(O)(OR$^{34'}$)$_2$, phosphate (—OP(O)(OR$^{34'}$)$_2$), phosphine (—PR$^{34'}$R$^{35'}$), phosphine oxide (—P(O)R$^{34'}$$_2$), sulfate (—OS(O)$_2$OR$^{34'}$), sulfoxide (S(O)R$^{34'}$), sulfonate (—S(O)$_2$OR$^{34'}$), sulfonyl (—S(O)$_2$R$^{34'}$), sulfonamide (—S(O)$_2$NR$^{34'}$R$^{35'}$), NO$_2$, boronic esters (—OB(OR$^{34'}$)$_2$), imino (—C=NR$^{34'}$R$^{35'}$)), borane radicals, stannane radicals, hydrazine radicals, hydrazone radicals, oxime radicals, nitroso groups, diazo groups, vinyl groups, sulfoximines, alanes, germanes, boroximes and borazines;

$R^{34'}$, $R^{35'}$, $R^{36'}$
are each independently substituted or unsubstituted $C_1$-$C_{20}$-alkyl, or substituted or unsubstituted $C_5$-$C_{30}$-aryl;

q', r' are each independently 0, 1, 2 or 3; where, in the case when q' or r' is 0, all substitutable positions of the aryl radical are substituted by hydrogen, where the radicals and indices in the group of the formula (c) X''', $R^{41'''}$, $R^{42'''}$, $R^{43'''}$, R$^{a'''}$, R$^{b'''}$, q''' and r''' are each independently as defined for the radicals and indices of the compounds of the general formula VI X', $R^{41'}$, $R^{42'}$, $R^{43'}$, R$^{a'}$, q' and r'. Suitable definitions for the aforementioned radicals and groups alkyl, aryl, heteroaryl, substituents with donor or acceptor action, alkoxy, aryloxy, alkylthio, arylthio, halogen, amino and amido are mentioned above.

Suitable meanings for the beforementioned radicals, units and groups alkyl, aryl, heteroaryl, groups with donor action or acceptor action, alkoxy, aryloxy, alkylthio, arylthio, halogen, amino and amido are mentioned before.

In a further embodiment the present invention concerns an inventive organic light emitting diode, wherein the compound of the general formula (VI) is a 3,6-disilyl substituted compound of the general formula (VIa):

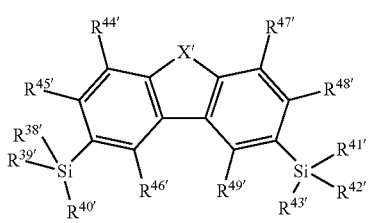

(VIa)

in which:
X' is NR$^{37'}$, S, O, PR$^{37'}$, SO$_2$ or SO; preferably NR$^{37'}$, S or O; more preferably NR$^{37'}$;

$R^{37'}$ is substituted or unsubstituted $C_1$-$C_{20}$-alkyl, substituted or unsubstituted $C_6$-$C_{30}$-aryl, or substituted or unsubstituted heteroaryl having from 5 to 30 ring atoms; preferably substituted or unsubstituted $C_6$-$C_{30}$-aryl or substituted or unsubstituted $C_1$-$C_{20}$-alkyl, more preferably substituted or unsubstituted $C_6$-$C_{10}$-aryl or unsubstituted $C_6$-$C_{10}$-aryl, most preferably substituted or unsubstituted phenyl, suitable substituents having been specified above;

$R^{38'}$, $R^{39'}$, $R^{40'}$, $R^{41'}$, $R^{42'}$, $R^{43'}$
are each independently substituted or unsubstituted $C_1$-$C_{20}$-alkyl or substituted or unsubstituted $C_6$-$C_{30}$-aryl or a structure of the general formula (c);
preferably at least one of the $R^{38'}$, $R^{39'}$ and $R^{40'}$ radicals and/or at least one of the $R^{41'}$, $R^{42'}$ and $R^{43'}$ radicals is substituted or unsubstituted $C_6$-$C_{30}$-aryl, more preferably substituted or unsubstituted $C_6$-$C_{10}$-aryl, most preferably substituted or unsubstituted phenyl, suitable substituents having been specified above, and/or one of the $R^{38'}$, $R^{39'}$ and $R^{40'}$ radicals and/or one of the $R^{41'}$, $R^{42'}$ and $R^{43'}$ radicals is a radical of the structure (c);

$R^{44'}$, $R^{45'}$, $R^{46'}$, $R^{47'}$, $R^{48'}$, $R^{49'}$
are each independently hydrogen or are as defined for R$^{a'}$ and R$^{b'}$, i.e. are each independently substituted or unsubstituted $C_1$-$C_{20}$-alkyl, substituted or unsubstituted $C_6$-$C_{20}$-aryl, substituted or unsubstituted heteroaryl having from 5 to 30 ring atoms or a substituent having donor or acceptor action, suitable substituents with donor or acceptor action having been specified above; preferably hydrogen, substituted or unsubstituted $C_1$-$C_6$-alkyl, substituted or unsubstituted $C_6$-$C_{10}$-aryl or SiR$^{34'}$R$^{35'}$R$^{36'}$; more preferably hydrogen, methyl, ethyl, phenyl, CF$_3$ or SiR$^{34'}$R$^{35'}$R$^{36'}$, where R$^{34'}$, R$^{35'}$ and R$^{36'}$ are preferably each independently substituted or unsubstituted $C_1$-$C_{20}$-alkyl or substituted or unsubstituted phenyl; more preferably, at least one of the R$^{34'}$, R$^{35'}$ and R$^{36'}$ radicals is substituted or unsubstituted phenyl; most preferably, at least one of the R$^{34'}$, R$^{35'}$ and R$^{36'}$ radicals is substituted phenyl, suitable substituents having been specified above;

and the further radicals and indices R$^{34'}$, R$^{35'}$, R$^{36'}$ are each as defined above.

In a particularly preferred embodiment, the compounds of the formula (VI) used in the inventive organic light-emitting diodes have the following definitions for the $R^{37'}$ to $R^{43'}$, R$^{a}$ and R$^{b}$ radicals and the X group:

X' is NR$^{37'}$,
$R^{37'}$ is substituted or unsubstituted $C_6$-$C_{30}$-aryl, preferably substituted or unsubstituted $C_6$-$C_{10}$-aryl, more preferably substituted or unsubstituted phenyl, suitable substituents having been specified above;

$R^{38'}$, $R^{39'}$, $R^{40'}$, $R^{41'}$, $R^{42'}$, $R^{43'}$
are each independently substituted or unsubstituted $C_1$-$C_{20}$-alkyl or substituted or unsubstituted $C_6$-$C_{30}$-aryl, or a structure of the general formula (c), preferably each independently substituted or unsubstituted $C_1$-$C_6$-alkyl or substituted or unsubstituted $C_6$-$C_{10}$-aryl, more preferably substituted or unsubstituted $C_1$-$C_6$-alkyl or substituted or unsubstituted phenyl; where, in one embodiment, at least one of the R$^{38'}$, R$^{39'}$ and R$^{40'}$ radicals and/or at least one of the R$^{41'}$, R$^{42'}$ and R$^{43'}$ radicals is substituted or unsubstituted $C_6$-$C_{30}$-aryl, preferably substituted or unsubstituted $C_6$-$C_{10}$-aryl, more preferably substituted or unsubstituted phenyl; preferred substituents having been specified above;

$R^{44'}$, $R^{45'}$, $R^{46'}$, $R^{47'}$, $R^{48'}$, $R^{49'}$
are each independently hydrogen or are each as defined for R$^{a'}$ and R$^{b'}$, i.e. are each independently substituted or unsubstituted $C_1$-$C_{20}$-alkyl, substituted or unsubstituted $C_6$-$C_{30}$-aryl, substituted or unsubstituted heteroaryl having from 5 to 30 ring atoms or a substituent having donor or acceptor action, suitable substituents with donor or acceptor action already having been specified above; preferably hydrogen, substituted or unsubstituted $C_1$-$C_6$-alkyl, substituted or unsubstituted $C_6$-$C_{10}$-aryl or SiR$^{34'}$R$^{35'}$R$^{36'}$; more preferably hydrogen, methyl, ethyl, phenyl, CF$_3$ or SiR$^{34'}$R$^{35'}$R$^{36'}$;

$R^{34'}$, $R^{35'}$, $R^{36'}$
are each independently substituted or unsubstituted $C_1$-$C_{20}$-alkyl or substituted or unsubstituted $C_6$-$C_{30}$-aryl, preferably substituted or unsubstituted $C_1$-$C_6$-alkyl or substituted or unsubstituted $C_6$-$C_{10}$-aryl, where R$^{34'}$, R$^{35'}$ and R$^{36'}$ are more preferably each independently substituted or unsubstituted $C_1$-$C_{20}$-alkyl or substituted or unsubstituted phenyl; more preferably, at least one of the $R^{34'}$, $R^{35'}$ and $R^{36'}$ radicals is substituted or unsubstituted phenyl; most preferably, at least one of the $R^{34'}$, $R^{35'}$ and $R^{36'}$ radicals is substituted phenyl, suitable substituents having been specified above.

A particularly preferred compound of formula (VI) is for example:

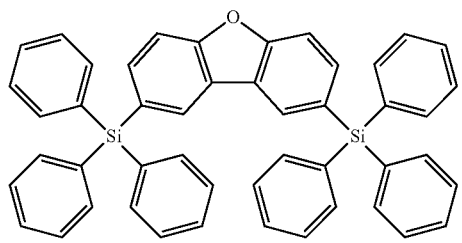 [SMILES: c1ccc([Si](c2ccccc2)(c2ccccc2)c2ccc3oc4ccc([Si](c5ccccc5)(c5ccccc5)c5ccccc5)cc4c3c2)cc1]

The compounds of formula (VI) may for example be prepared as described in the processes mentioned in WO2009/003898 or in analog processes.

The compounds of the general formula (VI) can be used as a matrix (diluent material), hole/exciton blocker, electron/exciton blocker, electron transport material or hole transport material in combination with the heteroleptic complexes claimed, which then serve as emitters. Inventive OLEDs which include both at least one compound of the formula (V) and a compound of the formula (I) exhibit particularly good efficiencies and lifetimes. Depending on the function in which the compound of the formula (VI) is used, it is present in pure form or in different mixing ratios. In a particularly preferred embodiment one or more compounds of formula (VI) are used as matrix material in the light emitting layer and/or as hole/exciton blockers.

The inventive OLEDs can be used in all devices in which electroluminescence is useful. Suitable devices are preferably selected from stationary and mobile visual display units and illumination means. The present invention therefore also relates to a device selected from the group consisting of stationary visual display units and mobile visual display units and illumination means, comprising an inventive OLED.

Stationary visual display units are, for example, visual display units of computers, televisions, visual display units in printers, kitchen appliances and advertising panels, illuminations and information panels. Mobile visual display units are, for example, visual display units in cellphones, smartphones, digital cameras, mp3 players, laptops, vehicles, and destination displays on buses and trains.

In addition, the inventive heteroleptic complexes of the general formula (I) can be used in OLEDs with inverse structure. The inventive complexes are preferably used in turn in these inverse OLEDs in the light-emitting layer. The structure of inverse OLEDs and the materials typically used therein are known to those skilled in the art.

EXAMPLES

The examples which follow, especially the methods, materials, conditions, process parameters, apparatus and the like, detailed in the examples, are intended to support the present invention, but not to restrict the scope of the present invention. In addition to the emitter 1 and emitter 2 complexes synthesized by way of example, it is possible to prepare further inventive metal-carbene complexes in an analogous manner using the appropriate starting compounds and reagents.

A. Synthesis

All synthesis steps are performed under protective gas atmosphere.

Synthesis Method:

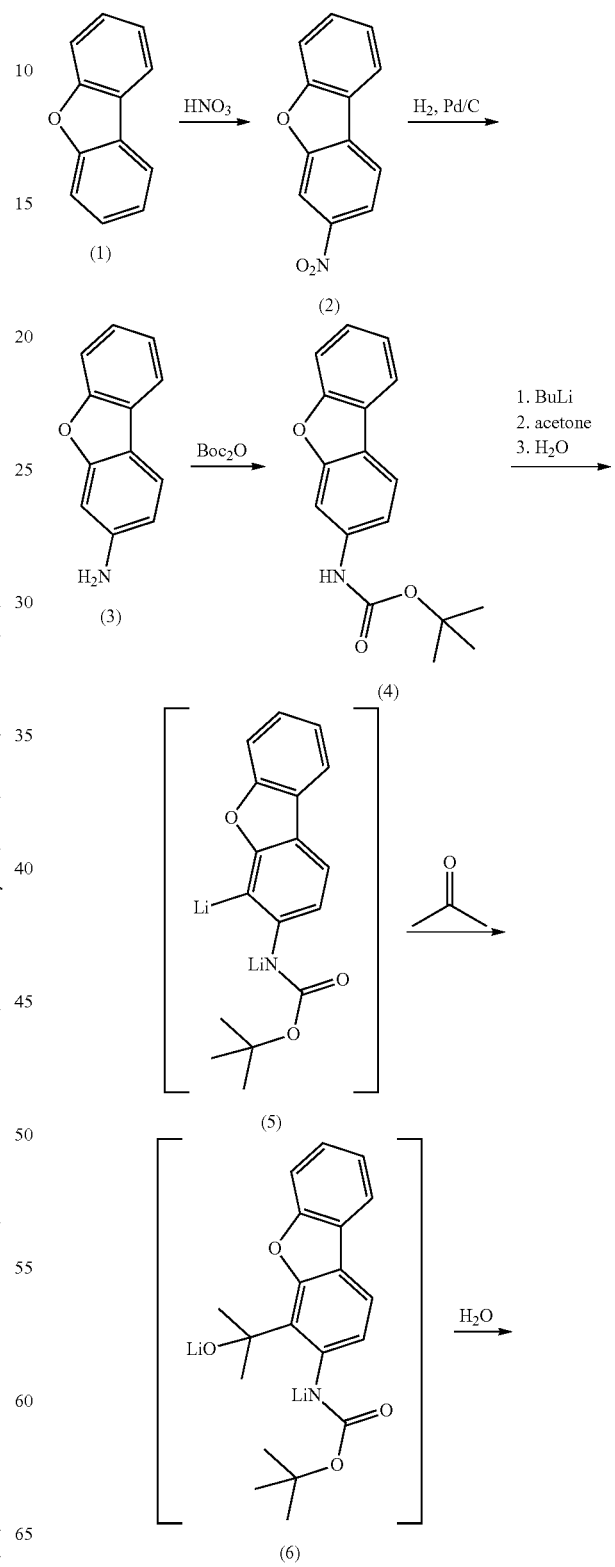

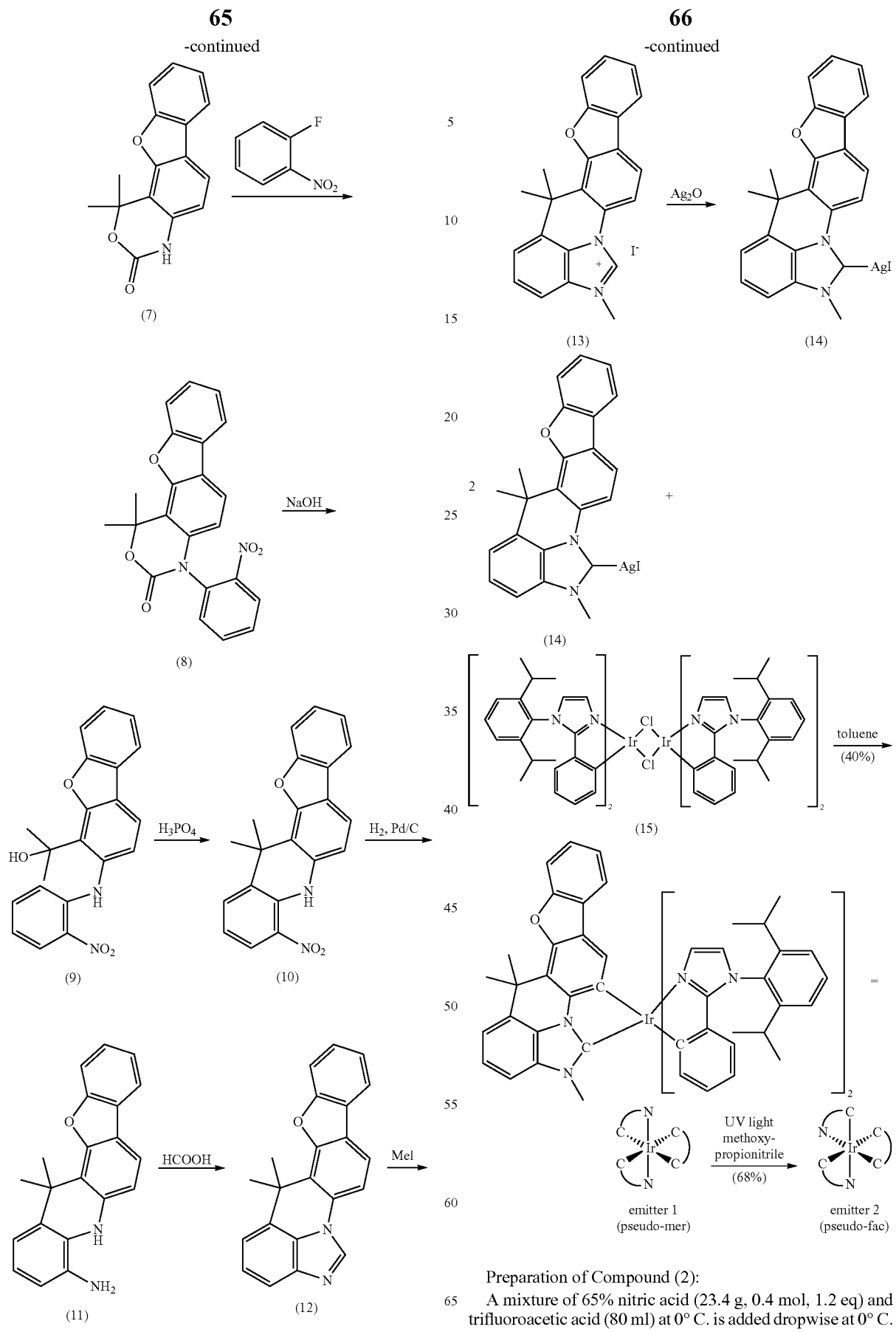
Preparation of Compound (2):
A mixture of 65% nitric acid (23.4 g, 0.4 mol, 1.2 eq) and trifluoroacetic acid (80 ml) at 0° C. is added dropwise at 0° C. to a suspension of 97% dibenzofuran (34.6 g, 0.2 mol, 1 eq)

and trifluoroacetic acid (420 ml) within one hour. At the end of the addition, the resulting solution is stirred at 0° C. for one hour, before being precipitated in 2 l of ice-water while stirring. Removal by suction filtration is followed by the dissolution of the crude material in dichloromethane and extraction with water. The organic phase is admixed with ethanol, and the dichloromethane is distilled out of the mixture. The concentration of the ethanolic suspension is followed by the removal by suction filtration and the washing of the product.

Yield: 38.3 g (90%).

$^1$H NMR ($d_6$-DMSO, 400 MHz): δ=7.47 (dd, 1H), 7.63 (dd, 1H), 7.78 (d, 1H), 8.25 (d, 1H), 8.27 (d, 1H), 8.37 (d, 1H), 8.57 (s, 1H).

Preparation of Compound (3):

The suspension of (2) (33.4 g, 156 mmol, 1 eq) in ethyl acetate (1.5 l) is stirred rapidly in a hydrogenation apparatus at room temperature and inertized with $N_2$. After addition of the Pd/C catalyst (10% Pd, 15 g, 14 mmol, 0.09 eq) and repeated inertization with $N_2$, full hydrogenation with $H_2$ is accomplished within a period of six hours. At the end of the slightly exothermic reaction (35° C.), the product is an almost completely dark solution. After filtration through Celite, the product is washed with ethyl acetate until the filtrate is colorless, and the filtrate is concentrated. Yield: 25.5 g (89%).

$^1$H NMR ($CD_2Cl_2$, 400 MHz): δ=3.97 (br s, 2H), 6.68 (d, 1H), 7.25 (dd, 1H), 7.30 (DD, 1H), 7.68 (d, 1H), 7.79 (d, 1H).

Preparation of Compound (4):

The reactant (3) (22.6 g, 123.3 mmol, 1 eq) is dissolved in dry tetrahydrofuran (500 ml) under an argon atmosphere, admixed with 98% di-tert-butyl dicarbonate (30.2 g, 135.7 mmol, 1.1 eq) and stirred at reflux overnight. The synthesis solution is concentrated almost completely, and the crude material containing residual moisture is stirred in 210 ml of n-hexane at 60° C. for a half hour. The suspension is filtered with suction while warm through a G3 frit. The residue is washed with n-hexane until the filtrate is colorless, and dried.

Yield: 31.3 g (90%).

$^1$H NMR ($CD_2Cl_2$, 360 MHz): δ=1.53 (s, 9H), 6.79 (br s, 1H), 7.17 (d, 1H), 7.32 (dd, 1H), 7.40 (dd, 1H), 7.53 (d, 1H), 7.82 (s, 1H), 7.85 (d, 1H), 7.88 (d, 1H).

Preparation of Compound (5):

A solution of 100 ml of 1.7 M tert-butyllithium in n-pentane (10.7 g, 166.5 mmol, 2.4 eq) at approx. −78° C. is added dropwise at a constant temperature of −78° C. within 45 min to a solution of (4) (20 g, 70.6 mmol, 1 eq) and anhydrous tetrahydrofuran (740 ml) while stirring under an argon atmosphere.

Preparation of Compound (6):

At −25° C., dry acetone at the same temperature was added to the resulting solution of the ortho-lithiated molecule (5) within 10 minutes, and the mixture was stirred at approx. −20° C. for seven hours. Subsequently, the solution was warmed gradually to room temperature overnight.

Preparation of Compound (7):

Compound (6) is converted to the product (7) by adding a distinct excess of ultrapure water. The synthesis mixture is filtered with suction, and the mother liquor is adjusted to pH 4 with 2 N hydrochloric acid (tritest pH paper) and stirred in 0.2 l of demineralized water at room temperature for one hour. The discharge of the organic phase is followed by extraction three times with water. The organic phase is dried over sodium sulfate and concentrated almost completely. The still moist light brown substance of mass 24 g is dissolved in two liters of dichloromethane, and the solution is dried over sodium sulfate. This anhydrous dichloromethane is concentrated on a Rotavapor down to approx. 0.2 l at 40° C. A suspension is obtained, which is stirred overnight with gentle stirring under protective gas (rubber balloon). This is followed by filtration with suction through a 75 ml G3 frit. The residue is washed with a little dichloromethane until the filtrate is water-clear, subjected to good suction drying and dried at 40° C. in a vacuum cabinet. The snow-white substance is present in a mass of 11.2 g and a yield of 59%.

$^1$H NMR ($d_6$-DMSO, 400 MHz): δ=1.80 (s, 6H), 6.90 (d, 1H), 7.33 (dd, 1H), 7.41 (dd, 1H), 7.64 (d, 1H), 7.95 (d, 1H), 7.99 (d, 1H), 10.49 (s, 1H).

Preparation of Compound (8):

The reactant (7) (11.1 g, 41.5 mmol) is dissolved in dimethylformamide, and the water-clear solution is admixed with 5.98 g (70.6 mmol, 1.03 eq) of o-fluoronitrobenzene. 14.9 g (46.9 mmol, 1.13 eq) of cesium carbonate are introduced into the pale yellow mixture, and the suspension is heated to 95° C. After about 15 hours, the reaction has ended. This is followed by the precipitation of the mother liquor at room temperature while stirring in 1 liter of demineralized water. The resulting pale yellow suspension is filtered with suction through a 125 ml G3 frit. After washing with 0.5 l of demineralized water, the residue is dried at 80° C. in a vacuum cabinet. The orange-yellow crystalline substance is very pure and has a mass of 15.73 g (98% yield).

$^1$H NMR ($CD_2Cl_2$, 360 MHz): δ=2.07 (s, 3H), 2.12 (s, 3H), 6.26 (d, 1H), 7.36 (dd, 1H), 7.47 (dd, 1H), 7.55 (d, 1H), 7.59 (dd, 1H), 7.70 (d, 1H), 7.74 (d, 1H), 7.83 (d, 1H), 7.88 (dd, 1H), 8.22 (d, 1H).

Preparation of Compound (9):

Suspended in 300 ml of ethanol and 96 ml of 5% sodium hydroxide solution (121.4 mmol, 3 eq), 15.7 g (40.4 mmol) of compound (8) are converted overnight under reflux (78° C.). The cooled suspension is filtered with suction, and the residue is washed with demineralized water until it is free of salts and pH-neutral. The finely crystalline product (9) dried at 78° C. in a vacuum cabinet is present in a mass of 13.15 g and a yield of 90%.

$^1$H NMR ($CD_2Cl_2$, 360 MHz): δ=1.94 (s, 6H), 2.70 (s, 1H), 6.81 (dd, 1H), 7.31 (dd, 1H), 7.39 (m, 3H), 7.45 (dd, 1H), 7.58 (d, 1H), 7.84 (d, 1H), 7.93 (d, 1H), 8.18 (d, 1H), 10.65 (s, 1H).

Preparation of Compound (10):

13.15 g (36.1 mmol) of the reactant (9) are suspended in a mixture of 300 ml of concentrated phosphoric acid and 9 ml of glacial acetic acid, and reacted at 125° C. within thirty hours. At the end of the reaction, the red-brown suspension cools while stirring. This is followed by pouring into one liter of stirred demineralized water, and filtration with suction through a blue-band filter. After washing with demineralized water until the pH is neutral, the brown-red residue is dried at 78° C. in a vacuum cabinet. 12.2 g (99% yield) of brown-red product (10) are obtained in very good purity.

$^1$H NMR ($CD_2Cl_2$, 360 MHz): δ=1.99 (s, 6H), 6.89 (d, 1H), 6.92 (dd, 1H), 7.33 (dd, 1H), 7.41 (dd, 1H), 7.58 (d, 1H), 7.75 (m, 2H), 7.87 (d, 1H), 8.09 (d, 1H), 10.33 (s, 1H).

Preparation of Compound (11):

In a hydrogenation apparatus, the nitro compound (10) is reacted with $H_2$ while stirring at room temperature within six hours. For this purpose, 10.0 g (29.0 mmol) of the reactant are suspended in 500 ml of ethyl acetate. To this is added a mixture of 4.9 g of the Pd/C catalyst (10% Pd, 4.6 mmol of Pd, 0.16 eq of Pd) in 10 ml of ethyl acetate. During the hydrogenation, soluble reactant is obtained, and a total of 1.95 l of hydrogen is consumed. The mixture is filtered through Celite using a fine fluted filter. The orange mother liquor is concentrated virtually completely. The still somewhat moist residue is stirred for a short time in 25 ml of a mixture of two parts by volume of tert-butyl methyl ether and one part by volume of petroleum ether. After filtration with suction and drying at 60°

C. in a drying cabinet, 7.75 g (86% yield) of brown crystals (11) are obtained in good purity.

$^1$H NMR (d$_6$-DMSO, 360 MHz): δ=1.86 (s, 6H), 4.84 (s, 2H), 6.50 (d, 1H), 6.62 (dd, 1H), 6.76 (d, 1H), 6.94 (d, 1H), 7.32 (m, 2H), 7.62 (d, 1H), 7.76 (d, 1H), 7.91 (d, 1H), 7.97 (s, 1H).

Preparation of Compound (12):

8.9 g (28.3 mmol) of the diamine (11) are converted in 50 ml of concentrated formic acid under reflux while stirring within three hours. The dark brown solution cools while stirring, and, after almost complete concentration on a Rotavapor, is admixed with 50 ml of ice-water and adjusted to pH 11 with sodium hydroxide solution.

Subsequently, it is extracted with dichloromethane, and the dichloromethane phase is dried over sodium sulfate and then concentrated. The mass of the crystalline product (12) present in good purity is 8.71 g (94.9% yield).

$^1$H NMR (CD$_2$Cl$_2$, 360 MHz): δ=2.05 (s, 6H), 7.36 (m, 3H), 7.48 (dd, 1H), 7.64, (m, 3H), 7.93 (dd, 2H), 8.55 (s, 1H).

Preparation of Compound (13):

8.7 g (26.8 mmol) of the benzimidazole (12) are converted in 30 ml of a solution of two parts by volume of tetrahydrofuran and one part by volume of iodomethane. The mass of the iodomethane used, of 22.8 g (160.63 mmol, 6 eq), corresponds to 10 ml, corresponding to one part by volume. The solution present at the start of the reaction is converted rapidly to a white suspension, which becomes very thick with increasing reaction time. This is therefore followed by dilution with 30 ml of tetrahydrofuran and further stirring at room temperature overnight. The suspension is filtered with suction and the residue is washed with tetrahydrofuran and finally with petroleum ether. After vacuum drying at 50° C., 11.1 g (89% yield) of light-brown crystalline iodide salt (13) are obtained.

$^1$H NMR (d$_6$-DMSO, 360 MHz): δ=2.07 (s, 6H), 4.19 (s, 3H), 7.51 (dd, 1H), 7.63 (dd, 1H), 7.87 (m, 2H), 7.95 (d, 1H), 7.97 (d, 1H), 8.15 (d, 1H), 8.24 (d, 1H), 8.44 (d, 1H), 10.68 (s, 1H).

Preparation of Compound (14):

0.224 g (0.480 mmol) of the iodide salt (13) are suspended in 10 ml of ultradry 1,4-dioxane in the presence of 1 g of 4 Å molecular sieve while stirring under argon at room temperature. The pale yellow suspension is admixed with 0.113 g (0.492 mmol, 1.025 eq) of silver(I) oxide in an argon countercurrent, and stirred at room temperature for two days under an argon atmosphere (rubber balloon). After the suspension cooled to 10° C. has been filtered with suction under argon, the residue present on the frit is washed with a little cold dioxane and subjected to good suction drying while continuing to pass argon over it. The masses of the molecular sieve present and of the 2.5% excess of silver(I) oxide are subtracted from this mixture of mass 1.321 g. This gives a calculated mass of 0.241 g (88% yield) of pure silver carbene (15).

$^1$H NMR (d$_6$-DMSO, 400 MHz): δ=1.92 (s, 12H), 2.05 (s, 3H), 2.07 (s, 3H), 6.88 (dd, 1H), 7.00 (d, 1H), 7.23 (d, 1H), 7.25 (d, 1H), 7.32 (dd, 1H), 7.38 (dd, 1H), 7.46 (d, 1H), 7.47 (d, 1H), 7.52 (d, 1H), 7.54 (d, 1H) 7.65 (dd, 1H), 7.67 (d, 1H), 7.79 (d, 1H), 7.81 (d, 1H), 7.95 (dd, 1H), 8.11 (d, 1H), 8.26 (dd, 1H), 8.53 (d, 1H).

Preparation of Compound (15):

0.39 g (1.11 mmol) of iridium(III) chloride trihydrate are dissolved in 11.5 ml of an argon-sparged solution consisting of three parts of 2-ethoxyethanol and one part of demineralized water, and also 0.71 g (2.33 mmol, 2.1 eq) of 1-(2',6'-diisopropylphenyl)-2-phenyl-1H-imidazole (synthesized analogously to Example 14 in WO 2006/121811) at room temperature while stirring. The dark green solution is refluxed. Shortly after attainment of reflux, a yellow substance precipitates out. After reaction overnight, the pale yellow suspension cools down and is filtered off with suction. The residue which had been washed with methanol and finally with n-pentane was vacuum-dried at 50° C. to obtain 0.76 g (82% yield) of the product (15).

$^1$H NMR (CD$_2$Cl$_2$, 400 MHz): δ=0.93 (d, 3H), 1.17 (d, 3H), 1.25 (d, 3H), 1.32 (d, 3H), 2.81 (m, 2H), 6.07 (d, 1H), 6.23 (d, 1H), 6.37 (dd, 1H), 6.51 (dd, 1H), 6.95 (s, 1H), 7.39 (m, 2H), 7.56 (d, 1H), 7.65 (s, 1H).

Emitter 1 (Pseudo-Mer Isomer):

The silver carbene (14) is added as a mixture to the stirred solution of 40 ml of extra-dry toluene and 2.29 g (1.37 mmol) of the iridium dichloro dimer (15), which has been initially charged under argon. In the mixture, which comprises molecular sieve and a very small amount of silver(I) oxide, there is calculated to be 2.36 g (2.06 mmol, 1.5 eq) of pure silver carbene. The synthesis mixture is stirred under reflux under an argon atmosphere (rubber balloon) overnight. After the mother liquor has been concentrated, it is chromatographed with acetonitrile using silica gel. Virtually clean fractions are combined and concentrated, and the resulting solid mixture is stirred in acetonitrile at room temperature overnight. After the suspension has been filtered with suction, the residue is filtered off with suction. It is washed with a little acetone, with acetonitrile and finally with petroleum ether. After suction drying, 1.57 g (46% yield) of clean pseudo-mer isomer are present in a purity by HPLC of 99.8%.

$^1$H NMR (CD$_2$Cl$_2$, 360 MHz): δ=0.70 (d, 3H), 0.84 (d, 3H), 1.00 (m, 11H), 1.19 (dd, 6H), 2.11 (m, 8H), 2.42 (m, 1H), 2.79 (m, 2H), 3.45 (s, 3H), 6.19 (d, 2H), 6.56 (m, 3H), 6.63 (dd, 3H), 6.77 (m, 3H), 7.20 (m, 4H), 7.32 (m, 7H), 7.49 (m, 3H), 7.60 (d, 1H).

Emitter 2 (Pseudo-Fac Isomer):

By means of photoisomerization with a TQ150 immersed medium-pressure mercury lamp in a nitrogen-inertized borosilicate glass reactor, the dissolved pseudo-mer isomer emitter 1 (1.55 g, 1.36 mmol) is converted to the pseudo-fac isomer emitter 2 in 450 ml of 3-methoxypropionitrile. During the two-hour irradiation, the solution is heated to 35° C. in the cooling water-cooled reactor with an aluminum foil jacket. This is followed by concentration of the pale yellow solution almost to dryness. The substance is stirred in a little acetone overnight. The suspension is filtered off with suction, and the residue is washed with a little acetone and dried at 60° C. under reduced pressure. This gives 1.05 g (68% yield) of the pseudo-fac isomer which has a purity by HPLC of 98.4%.

$^1$H NMR (CD$_2$Cl$_2$, 500 MHz): δ=0.77 (d, 3H), 0.83 (d, 3H), 0.88 (d, 3H), 0.93 (D, 3H), 0.97 (d, 3H), 1.07 (d, 3H), 1.19 (d, 3H), 1.22 (d, 3H), 1.94 (m, 1H), 2.02 (s, 3H), 2.12 (s, 3H), 2.47 (m, 1H), 2.58 (m, 1H), 2.79 (m, 1H), 3.65 (s, 3H), 6.12 (d, 1H), 6.20 (d, 1H), 6.38 (dd, 1H), 6.49 (m, 2H), 6.62 (d, 1H), 6.68 (m, 2H), 6.78 (d, 1H), 6.79 (d, 1H), 6.81 (d, 1H), 6.96 (d, 1H), 7.05 (s, 1H), 7.12 (m, 2H), 7.28 (m, 4H), 7.35 (dd, 3H), 7.50 (m, 4H).

High-resolution spectroscopy by means of LC/MS coupling gave, for the protonated molecular ion (M+H)$^+$: 1135.48 (M$^+$, correct isotope pattern).

B. Diode Example

Example 1

Production of an OLED

The ITO substrate used as the anode is first cleaned with commercial detergents for LCD production (Deconex®

20NS, and 250RGAN-ACID® neutralizing agent) and then in an acetone/isopropanol mixture in an ultrasound bath. To eliminate any possible organic residues, the substrate is exposed to a continuous ozone flow in an ozone oven for a further 25 minutes. This treatment also improves the hole injection properties of the ITO. Next, the hole injection layer, AJ20-1000 from Plexcore, is spun on from solution.

Thereafter, the organic materials mentioned hereinafter are applied by vapor deposition to the cleaned substrate at a rate of approx. 0.5-5 nm/min at about $10^{-7}$-$10^{-9}$ mbar. The hole conductor and exciton blocker applied to the substrate is Ir(DPBIC)$_3$

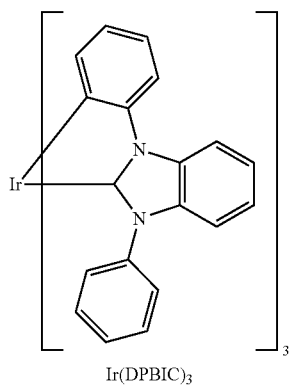

Ir(DPBIC)$_3$ with a thickness of 45 nm, the first 35 nm of which are doped with MoO$_x$ to improve the conductivity.

Subsequently, a mixture of the unbridged emitter CEm (as a comparison; prepared analogously to the above-described synthesis with the corresponding unbridged carbene precursor compound)

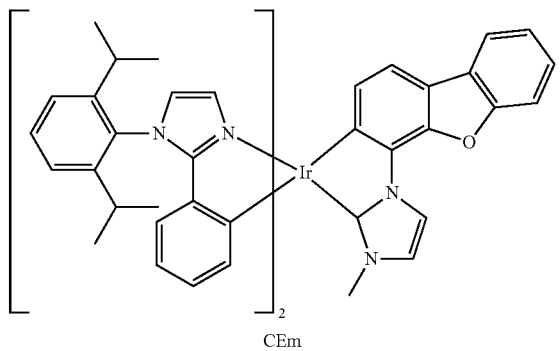

CEm or the bridged inventive emitter 2 and the compound Ma

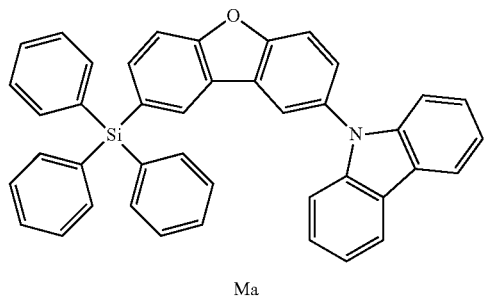 [SMILES: c1ccc([Si](c2ccccc2)(c2ccccc2)c2ccc3oc4ccc(-n5c6ccccc6c6ccccc65)cc4c3c2)cc1]

Ma (the synthesis of this compound is described in prior international application PCT/EP2009/067120) is applied by vapor deposition as a matrix material with a thickness of 40 nm. Subsequently, the matrix material Ma is once again applied by vapor deposition with a thickness of 10 nm as an exciton and hole blocker.

Next, an electron transporter BCP (2,9-dimethyl-4,7-diphenyl-1,10-phenanthroline) is applied by vapor deposition in a thickness of 20 nm, as are a 0.75 nm-thick lithium fluoride layer and finally a 100 nm-thick Al electrode. All components are adhesive-bonded to a glass lid in an inert nitrogen atmosphere.

To characterize the OLED, electroluminescence spectra are recorded at different currents and voltages. In addition, the current-voltage characteristic is measured in combination with the light output emitted. The light output can be converted to photometric parameters by calibration with a photometer. The lifetime $t_{1/2}$ of the diode is defined by the time which passes until the luminance has fallen to 50% of its initial value. The lifetime measurement is carried out at a constant current.

The following electrooptical data are obtained:

| Emitter | CIE | EQE @ 300 nits | $t_{1/2}$ @ 300 nits (normalized to the value of CEm) |
| --- | --- | --- | --- |
| CEm | 0.17/0.25 | 14% | 100% |
| Emitter 2 | 0.16/0.25 | 11% | 150% |

With the bridged inventive emitter 2, a better device lifetime is obtained compared to the unbridged emitter Cem.

Example 2

A diode comprising the following layer sequence is prepared:

ITO-AJ20-1000—35 nm Ir(DPBIC)$_3$ (90 wt.-%) mixed with 10 wt.-% MoO$_x$—10 nm Ir(DPBIC)$_3$—40 nm Ma (80 wt.-%) mixed with 20 wt.-% Emitter 2—10 nm Ma—20 nm BCP (80 wt.-%) mixed with 20 wt.-% Ma 2—1 nm LiF—100 nm Al.

The diode is prepared analog to the diode example mentioned above (example 1).

A light emitting diode comprising the following CIE values is obtained: 0.16; 0.25 (EQE @ 300 nits: 11%).

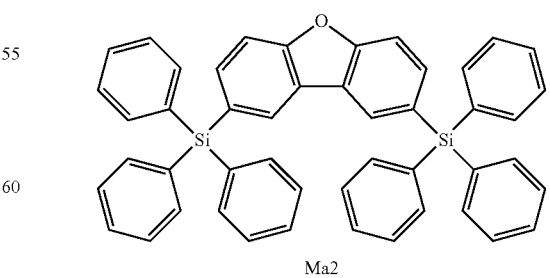

Ma2

The synthesis of Ma2 is for example described in WO 2009/003898, example 4 g, p. 89.

Example 3

A diode comprising the following layer sequence is prepared:

ITO-AJ20-1000—35 nm Ir(DPBIC)$_3$ (90 wt.-%) mixed with 10 wt.-% MoO$_x$—10 nm Ir(DPBIC)$_3$—40 nm Ma 3 (80 wt.-%) mixed with 20 wt.-% Emitter 2—10 nm Ma 2—20 nm BCP (80 wt.-%) mixed with 20 wt.-% LiQ—1 nm LiQ—100 nm Al.

The diode is prepared analog to the diode example mentioned above (example 1).

A light emitting diode comprising the following CIE values is obtained: 0.16; 0.25 (EQE @ 300 nits: 9%).

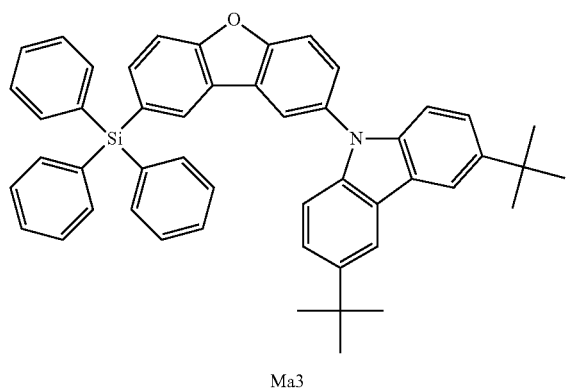 [SMILES: CC(C)(C)c1ccc2c(c1)c1cc(C(C)(C)C)ccc1n2-c1ccc2oc3ccc([Si](c4ccccc4)(c4ccccc4)c4ccccc4)cc3c2c1]

Ma3

The synthesis of Ma3 is for example described in WO 2010/079051, compound 22, p. 87.

Example 4

A diode comprising the following layer sequence is prepared:

ITO-AJ20-1000—35 nm Ir(DPBIC)$_3$ (90 wt.-%) mixed with 10 wt.-% MoO$_x$—10 nm Ir(DPBIC)$_3$—40 nm Ma 4 (75 wt.-%) mixed with 25 wt.-% Emitter 2—10 nm Ma 4—20 nm BCP (50 wt.-%) mixed with 50 wt.-% Ma—1 nm LiF—100 nm Al.

The diode is prepared analog to the diode example mentioned above (example 1).

A light emitting diode comprising the following CIE values is obtained: 0.17; 0.29 (Voltage @ 300 nits: 3.8 V).

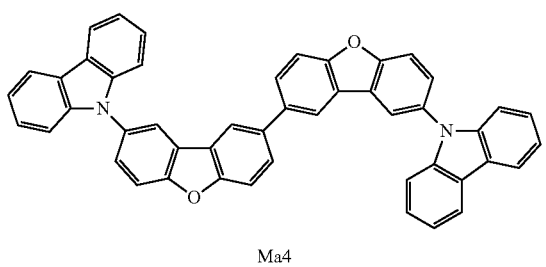 [SMILES: c1ccc2c(c1)c1ccccc1n2-c1ccc2oc3ccc(-c4ccc5oc6ccc(-n7c8ccccc8c8ccccc87)cc6c5c4)cc3c2c1]

Ma4

The synthesis of Ma4 is for example described in WO 2007/077810.

The invention claimed is:

1. A metal-carbene complex of formula (I):

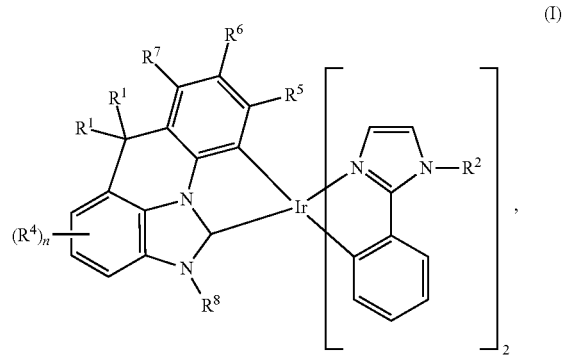

wherein:
each $R^1$ is independently hydrogen, a linear or branched alkyl radical having 1 to 20 carbon atoms, which is optionally interrupted by at least one heteroatom and optionally bears at least one functional group, a cycloalkyl radical having 3 to 20 carbon atoms, which is optionally interrupted by at least one heteroatom and optionally bears at least one functional group, a substituted or unsubstituted aryl radical having 6 to 30 carbon atoms and optionally bearing at least one functional group, a substituted or unsubstituted heteroaryl radical having a total of 5 to 18 carbon atoms and heteroatoms and optionally bears at least one functional group, or the two $R^1$ radicals, together with the carbon atom to which they are bonded, form a substituted or unsubstituted $C_5$, $C_6$, $C_7$, or $C_8$ ring;

$R^5$ and $R^6$ together, or $R^6$ and $R^7$ together, form a unit of the formula:

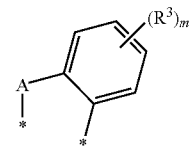

wherein * denotes the connection to the carbon atoms of the benzene ring bearing the $R^5$ and $R^6$ radicals or $R^6$ and $R^7$ radicals, and the A is connected to the carbon atom bearing the $R^5$, $R^6$, or $R^7$ radical, A is oxygen or sulfur;

$R^2$ is a linear or branched alkyl radical having 1 to 20 carbon atoms, which is optionally interrupted by at least one heteroatom and optionally bears at least one functional group, a cycloalkyl radical having 3 to 20 carbon atoms, which is optionally interrupted by at least one heteroatom and optionally bears at least one functional group, a substituted or unsubstituted aryl radical having 6 to 30 carbon atoms and optionally bearing at least one functional group, a substituted or unsubstituted heteroaryl radical having a total of 5 to 18 carbon atoms and/or heteroatoms and optionally bearing at least one functional group;

$R^3$ and $R^4$ are each independently a linear or branched alkyl radical having 1 to 20 carbon atoms, which is optionally interrupted by at least one heteroatom and optionally bears at least one functional group, a cycloalkyl radical having 3 to 20 carbon atoms, which is optionally interrupted by at least one heteroatom and optionally bears at least one functional group, a substituted or unsubstituted aryl radical having 6 to 30 carbon atoms and optionally bearing at least one functional group, a substituted or unsubstituted heteroaryl radical having a total of 5 to 18 carbon atoms and/or heteroatoms and optionally bearing at least one functional group;

$R^8$ is a linear or branched alkyl radical having 1 to 4 carbon atoms; and m and n are each independently 0, 1, 2, or 3.

2. The metal-carbene complex of claim 1, wherein, in formula (I):
each $R^1$ is independently a linear or branched alkyl radical having 1 to 10 carbon atoms, a substituted or unsubstituted aryl radical having 6 to 30 carbon atoms, or the two R1 radicals, together with the carbon atom to which they are bonded, form a substituted or unsubstituted C5 or C6 ring;

$R^5$ and $R^6$ together, or $R^6$ and $R^7$ together, form a unit of the formula:

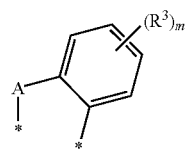

wherein * denotes the connection to the carbon atoms of the benzene ring bearing the $R^5$ and $R^6$ radicals or $R^6$ and $R^7$ radicals, and the A is connected to the carbon atom bearing the $R^5$, $R^6$ or $R^7$ radical;

A is oxygen or sulfur;

$R^2$ is an ortho,ortho'-disubstituted aryl radical having 6 to 30 carbon atoms;

$R^3$ and $R^4$ are each a linear or branched alkyl radical having 1 to 10 carbon atoms;

$R^8$ is a linear or branched alkyl radical having 1 to 4 carbon atoms; and m and n are each independently 0, 1, or 2.

3. The metal-carbene complex of claim 1, wherein, in formula (I):
each $R^1$ is independently a linear or branched alkyl radical having 1 to 4 carbon atoms;

$R^6$ and $R^7$ together form a unit of the formula:

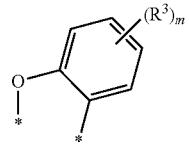

wherein * denotes the connection to the carbon atoms of the benzene ring bearing the $R^6$ and $R^7$ radicals, and the oxygen atom is connected to the carbon atom bearing the $R^7$ radical;

$R^2$ is an ortho,ortho'-dialkylated phenyl radical;

$R^3$ and $R^4$ are each a linear or branched alkyl radical having 1 to 4 carbon atoms;

$R^8$ is a linear or branched alkyl radical having 1 to 4 carbon atoms; and m and n are each independently 0, 1 or 2.

4. A light-emitting layer comprising a metal-carbene complex of claim 1.

5. An organic light-emitting diode comprising a light-emitting layer of claim 4.

6. A device selected from the group consisting of stationary visual display units, mobile visual display units, and illumination means, comprising an organic light-emitting diode of claim 5.

7. A device selected from the group consisting of stationary visual display units, mobile visual display units, and illumination means, comprising a light-emitting layer of claim 4.

8. An organic light-emitting diode comprising a metal-carbene complex of claim 1, and at least one compound of the formula (V):

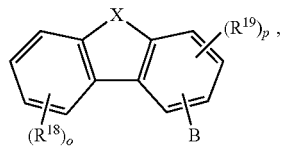

wherein:
X is NR, S, O, or PR, wherein R is aryl, heteroaryl, alkyl, cycloalkyl, or heterocycloalkyl;

$R^{18}$ and $R^{19}$ are each independently alkyl, cycloalkyl, heterocycloalkyl, aryl, heteroaryl, $SiR^{15}R^{16}R^{17}$, a group B or a group with donor or acceptor action;

o is 0, 1, 2, 3, or 4;

p is 0, 1, 2, or 3;

B is $-NR^{20}R^{21}$, $-P(O)R^{22}R^{23}$, $-PR^{24}R^{25}$, $-S(O)_2R^{26}$, $-S(O)R_{27}$, $-SR^{28}$, or $-OR^{29}$;

$R^{20}$ and $R^{21}$ form, together with the nitrogen atom, a cyclic radical having 3 to 10 ring atoms, which is optionally substituted by one or more substituents selected from alkyl, cycloalkyl, heterocycloalkyl, aryl, heteroaryl, and a group with donor or acceptor action, and/or optionally fused to one or more further cyclic radicals having 3 to 10 ring atoms, where the fused radicals are optionally substituted by one or more substituents selected from alkyl, cycloalkyl, heterocycloalkyl, aryl, heteroaryl and a group with donor or acceptor action; and $R^{15}$, $R^{16}$, $R^{17}$, $R^{22}$, $R^{23}$, $R^{24}$, $R^{25}$, $R^{26}$, $R^{27}$, $R^{28}$, and $R^{29}$ are each independently aryl, heteroaryl, alkyl, cycloalkyl, or heterocycloalkyl, or two units of formula (V) are linked via a linear or branched, saturated or unsaturated bridge, which is optionally interrupted by at least one hetero atom, via a bond, or via O.

9. The organic light-emitting diode of claim 8, which comprises an emission layer comprising the metal-carbene complex, at least one matrix material of the formula (V), and at least one further hole-transporting matrix material.

10. A device selected from the group consisting of stationary visual display units, mobile visual display units, and illumination means, comprising an organic light-emitting diode of claim 8.

11. An organic light-emitting diode comprising a metal-carbene complex of claim 1, and at least one compound of the formula (II):

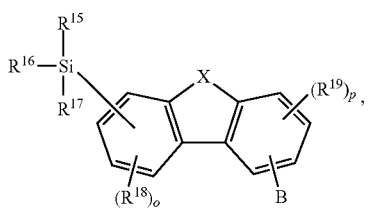

(II)

wherein:
X is NR, S, O, or PR, where wherein R is aryl, heteroaryl, alkyl, cycloalkyl, or heterocycloalkyl each having a total of 1 to 30 carbon atoms and/or heteroatoms;

B is —$NR^{20}R^{21}$, —$P(O)R^{22}R^{23}$, —$PR^{24}R^{25}$, —$S(O)_2R^{26}$, —$S(O)R^{27}$, —$SR^{28}$, or —$OR^{29}$;

$R^{22}$, $R^{23}$, $R^{24}$, $R^{25}$, $R^{26}$, $R^{27}$, $R^{28}$ and $R^{29}$ are each independently aryl, heteroaryl, alkyl, cycloalkyl, or heterocycloalkyl each having a total of 1 to 40 carbon atoms and/or heteroatoms;

$R^{15}$, $R^{16}$, and $R^{17}$ are each independently aryl, heteroaryl, alkyl, cycloalkyl, or heterocycloalkyl each having a total of 1 to 20 carbon atoms and/or heteroatoms, wherein at least one of the $R^{15}$, $R^{16}$, and $R^{17}$ radicals is aryl or heteroaryl;

$R^{18}$ and $R^{19}$ are each independently alkyl, cycloalkyl, heterocycloalkyl, aryl, or heteroaryl each having a total of 1 to 20 carbon atoms and/or heteroatoms and/or a B group and/or a group with donor or acceptor action; and o and p are each independently 0, 1, 2, or 3;

$R^{20}$ and $R^{21}$ form, together with the nitrogen atom, a cyclic radical having 3 to 10 ring atoms, which is optionally substituted by one or more substituents selected from alkyl, cycloalkyl, heterocycloalkyl, aryl, heteroaryl, and a group with donor or acceptor action, and/or may be fused to one or more further cyclic radicals having 3 to 10 ring atoms, wherein the fused radicals may be unsubstituted or substituted by one or more substituents selected from alkyl, cycloalkyl, heterocycloalkyl, aryl, heteroaryl, and a group with donor or acceptor action.

12. An organic light-emitting diode comprising a metal-carbene complex of claim 1, and at least one compound of the formula (VI):

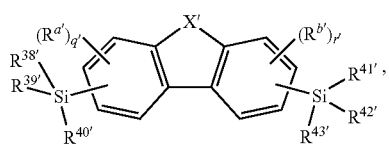

(VI)

wherein:
X' is $NR^{37'}$, S, O, $PR^{37'}$, $SO_2$ or SO;
$R^{37'}$ is substituted or unsubstituted $C_1$-$C_{20}$-alkyl, substituted or unsubstituted $C_6$-$C_{30}$-aryl, or substituted or unsubstituted heteroaryl having from 5 to 30 ring atoms;

$R^{38'}$, $R^{39'}$, $R^{40'}$, $R^{41'}$, $R^{42'}$, and $R^{43'}$ are each independently substituted or unsubstituted $C_1$-$C_{20}$-alkyl, substituted or unsubstituted $C_6$-$C_{30}$-aryl, or a structure of formula (c):

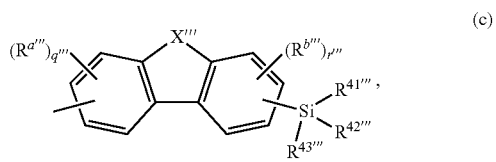

(c)

$R^{a'}$ and $R^{b'}$ are each independently substituted or unsubstituted substituted or unsubstituted $C_6$-$C_{30}$-aryl, or substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^{34'}R^{35'}R^{36'}$, halogen radicals, halogenated $C_1$-$C_{20}$-alkyl radicals, carbonyl (—$CO(R^{34'})$), carbonylthio (—C═$O(SR^{34'})$), carbonyloxy (—C═$O(OR^{34'})$), oxycarbonyl (—OC═$O(R^{34'})$), thiocarbonyl (—SC═O($R^{34'}$)), amino (—$NR^{34'}R^{35'}$), OH, pseudohalogen radicals, amido (—C═$O(NR^{34'})$), —$NR^{34'}C$═$O(R^{35'})$, phosphonate (—$P(O)(OR^{34'})_2$, phosphate (—OP(O)($OR^{34'})_2$), phosphine (—$PR^{34'}R^{35'}$), phosphine oxide (—$P(O)R^{34'}_2$), sulfate (—$OS(O)_2OR^{34'}$), sulfoxide ($S(O)R^{34'}$), sulfonate (—$S(O)_2OR^{34'}$), sulfonyl (—$S(O)_2R^{34'}$), sulfonamide (—$S(O)_2NR^{34'}R^{35'}$), $NO_2$, boronic esters (—$OB(OR^{34'})_2$), imino (—C═$NR^{34'}R^{35'}$)), borane radicals, stannane radicals, hydrazine radicals, hydrazone radicals, oxime radicals, nitroso groups, diazo groups, vinyl groups, sulfoximines, alanes, germanes, boroximes, and borazines;

$R^{34'}$, $R^{35'}$, $R^{36'}$ are each independently substituted or unsubstituted $C_1$-$C_{20}$-alkyl, or substituted or unsubstituted $C_6$-$C_{30}$-aryl; and q' and r' are each independently 0, 1, 2, or 3; wherein, in the case when q' or r' is 0, all substitutable positions of the aryl radical are substituted by hydrogen, wherein the radicals and indices in the group of the formula (c) X''', $R^{41'''}$, $R^{42'''}$, $R^{43'''}$, $R^{a'''}$, $R^{b'''}$, q''', and r''' are each independently as defined for the radicals and indices of the compounds of the general formula (VI) X', $R^{41'}$, $R^{43'}$, $R^{a'}$, $R^{b'}$, q', and r'.

13. The organic light-emitting diode of claim 12, which comprises an emission layer comprising the metal-carbene complex, at least one matrix material of the formula (VI), and at least one further hole-transporting matrix material.

14. An organic light-emitting diode comprising a metal-carbene complex of claim 1.

15. The organic light-emitting diode of claim 14, wherein the metal-carbene complex is present as an emitter, matrix material, charge transport material, and/or charge blocker.

* * * * *